(12) United States Patent
Hasegawa et al.

(10) Patent No.: US 8,465,418 B2
(45) Date of Patent: Jun. 18, 2013

(54) CAPSULE-TYPE MEDICAL DEVICE

(75) Inventors: Jun Hasegawa, Hino (JP); Tetsuo Nonami, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1281 days.

(21) Appl. No.: 12/252,085

(22) Filed: Oct. 15, 2008

(65) Prior Publication Data

US 2009/0043164 A1   Feb. 12, 2009

Related U.S. Application Data

(63) Continuation of application No. PCT/JP2007/058355, filed on Apr. 17, 2007.

(30) Foreign Application Priority Data

Apr. 19, 2006   (JP) .................................. 2006-115958

(51) Int. Cl.
*A61B 1/00* (2006.01)
*A61B 1/04* (2006.01)

(52) U.S. Cl.
USPC ........................................................ 600/117

(58) Field of Classification Search
USPC .................. 600/109, 117, 118, 160
See application file for complete search history.

(56) References Cited

U.S. PATENT DOCUMENTS

| 5,395,366 | A | 3/1995 | D'Andrea et al. |
| 2003/0073935 | A1* | 4/2003 | Segawa et al. ................ 600/593 |
| 2003/0195415 | A1* | 10/2003 | Iddan ............................. 600/424 |
| 2003/0216622 | A1 | 11/2003 | Meron et al. |
| 2004/0054278 | A1 | 3/2004 | Kimchy et al. |
| 2004/0236180 | A1* | 11/2004 | Uchiyama et al. ............. 600/109 |
| 2005/0148816 | A1 | 7/2005 | Glukhovsky et al. |
| 2006/0063974 | A1* | 3/2006 | Uchiyama et al. ............. 600/114 |
| 2006/0202998 | A1 | 9/2006 | Hirakawa et al. |
| 2007/0060798 | A1* | 3/2007 | Krupnik et al. ................ 600/300 |
| 2007/0078300 | A1* | 4/2007 | Zinaty et al. .................. 600/102 |
| 2007/0078335 | A1* | 4/2007 | Horn ............................. 600/425 |

FOREIGN PATENT DOCUMENTS

| EP | 0 662 304 A1 | 7/1995 |
| EP | 0 667 115 A1 | 8/1995 |
| EP | 1 690 491 A1 | 8/2006 |
| JP | 2003-524448 | 8/2003 |
| JP | 2005-198789 | 7/2005 |
| JP | 2005-218584 | 8/2005 |

(Continued)

OTHER PUBLICATIONS

Saito, Nobuo, et al., "Data Structures and Algorithms", pp. 124-129, Corona Publishing Co., Ltd.
Extended Supplementary European Search Report dated Dec. 18, 2009.

*Primary Examiner* — Philip R Smith
(74) *Attorney, Agent, or Firm* — Scully, Scott, Murphy & Presser, P.C.

(57) ABSTRACT

The position of an antenna incorporated in a capsule-type endoscope 3 that moves in a body is estimated using a plurality of antennae, and where the distance dij between two positions Pti and P(t−1)j estimated at adjacent times falls within a predetermined value, pieces of information for these positions are related to each other and stored in a memory as connection information. Subsequently, processing for searching for a route from the connection information stored in the memory and calculating a track is performed.

4 Claims, 15 Drawing Sheets

FOREIGN PATENT DOCUMENTS

| WO | WO 00/22975 | 4/2000 |
| WO | WO 2004/045374 A2 | 6/2004 |
| WO | WO 2005/053518 A1 | 6/2005 |
| WO | WO 2006/077529 A2 | 7/2006 |

* cited by examiner

FIG.17

| t \ k | 1 | 2 | 3 | 4 | 5 | 6 | ... |
|---|---|---|---|---|---|---|---|
| 1 | Rxyz11 | Rxyz12 | | | | | |
| 2 | Rxyz21 | | Rxyz22 | | | | |
| 3 | Rxyz31 | | Rxyz32 | Rxyz33 | | | |
| 4 | Rxyz41 | | Rxyz42 | | | | |
| ... | | | | | | | |
| tend | Rxyztend 1 | | Rxyztend 2 | | | Rxyztend 3 | |

FIG.19

| t \ | tend | tend-1 | tend-2 | ... | 3 | 2 | 1 |
|---|---|---|---|---|---|---|---|
| 1 | Rxyztend 1 | Rxyztend-11 | Rxyztend-21 | ... | | Rxyz21 | Rxyz11 |
| 2 | Rxyztend 2 | Rxyztend-12 | Rxyztend-22 | ... | Rxyz31 | Rxyz22 | |
| 3 | Rxyztend 3 | Rxyztend-13 | | ... | Rxyz32 | | |
| 4 | | | Rxyztend-23 | ... | | | |
| ... | | | | ... | Rxyz33 | | |
| N-1 | | | | ... | | | |
| N | | | | ... | | | Rxyz12 |

CAPSULE-TYPE MEDICAL DEVICE

CROSS REFERENCE TO RELATED APPLICATION

This application is a continuation application of PCT/JP2007/058355 filed on Apr. 17, 2007 and claims benefit of Japanese Application No. 2006-115958 filed in Japan on Apr. 19, 2006, the entire contents of which are incorporated herein by this reference.

BACKGROUND OF THE INVENTION

1. Field of the Invention

The present invention relates to a capsule-type medical device that is inserted to a living body to perform image pickup, etc.

2. Description of the Related Art

Endoscopes, which enable diagnostic examinations, or treatments as necessary, of a body cavity by inserting an insertion portion to the body cavity have come into wide use in the medical and other fields.

Also, recently, a capsule-type medical device including a capsule-type in-vivo device having the shape of a capsule (abbreviated to "capsule"), which is swallowed from the mouth to pick up images in the body cavity, thereby enabling an endoscopic examination, has been put into practical use.

When a capsule is inserted into a body cavity, it ordinarily moves in the body cavity by means of peristaltic movement or the like, and accordingly, it is sometimes desirable to know information obtained by the capsule corresponds to which site in the body.

Therefore, as a first related art example, for example, Japanese Patent Application Laid-Open Publication No. 2003-524448 discloses the art in which a signal sent wirelessly from a capsule in a body cavity via an antenna is received by a plurality of antennae arranged outside the body to calculate the position of the capsule from, e.g., the intensity of the received signal.

Also, as a second related art example, Japanese Patent Application Laid-Open Publication No. 2005-198789 discloses the art in which a signal sent wirelessly via an antenna of a capsule in a body cavity is received by a plurality of antennae arranged outside the body to calculate the position and direction of the capsule from, e.g., the intensity of the received signal.

Meanwhile, when the position of a capsule is estimated, multiple positions may be estimated because of noise, etc.

Where multiple positions have been estimated as mentioned above, it is difficult to determine the track of the movement of the capsule unless the positions of the antenna in the capsule at respective times are determined, lowering the utility value of information on the inside of the body, etc., obtained by the capsule.

SUMMARY OF THE INVENTION

A capsule-type medical device according to the present invention includes: a capsule-type in-vivo device including an antenna, the capsule-type in-vivo device being inserted into a living body; a wireless transmission section for transmitting wirelessly an electromagnetic wave signal from the antenna in the capsule-type in-vivo device; a plurality of extracorporeal antennae arranged outside the living body; an estimation section for estimating a position of the antenna or the capsule-type in-vivo device from the electromagnetic wave signal at a time when the electromagnetic wave signal was received by the plurality of extracorporeal antennae; and a track calculating section for calculating a track of movement of the capsule-type in-vivo device according to a condition set for the case where a plurality of positions at mutually different times have been estimated by the estimation section.

BRIEF DESCRIPTION OF THE DRAWINGS

FIG. 17 is a diagram illustrating two-dimensional array information stored in a second memory as a result of the processing in FIG. 16;

FIG. 19 is a diagram illustrating two-dimensional array information stored in a third memory as a result of the processing in FIG. 18.

DESCRIPTION OF THE PREFERRED EMBODIMENT(S)

Hereinafter, embodiments of the present invention will be described with reference to the drawings.

Embodiment 1

Figure 1A:
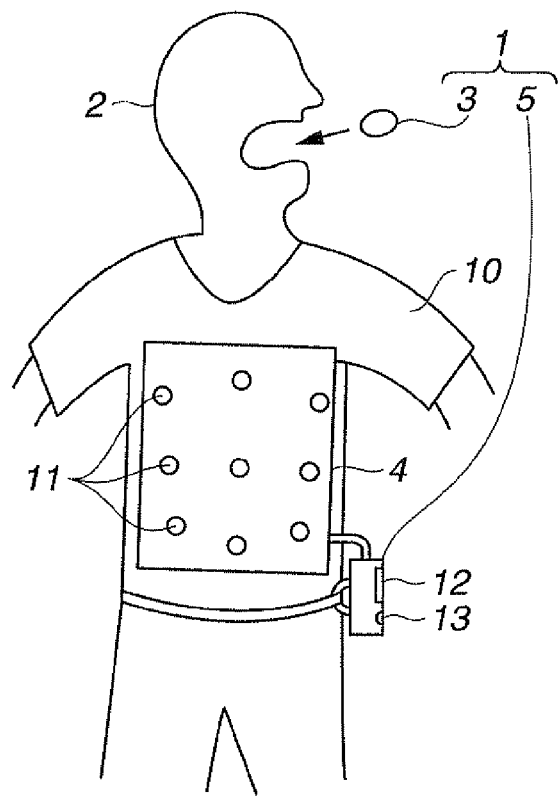
FIG. 1A is a diagram illustrating a configuration of a capsule-type endoscopic device, etc., according to embodiment 1 of the present invention.
Figure 1B:
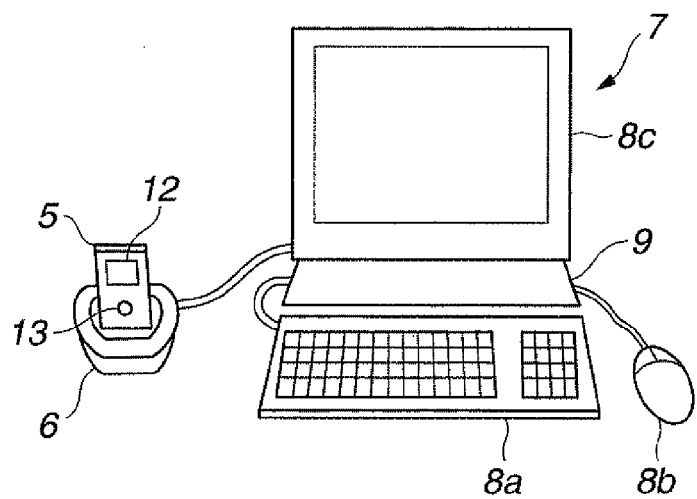
FIG. 1B is a diagram illustrating a state in which an extracorporeal device in FIG. 1A is connected to a terminal apparatus.
Figure 2:
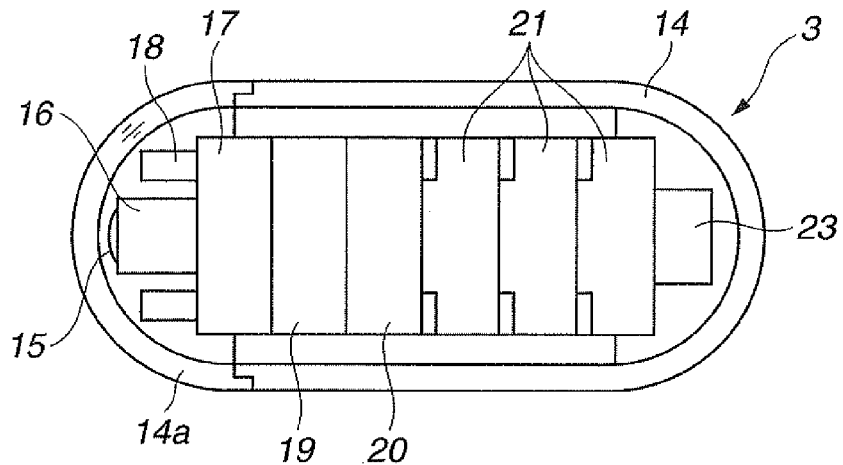
FIG. 2 is a schematic cross-sectional view of an inner configuration of a capsule-type endoscope.
Figure 3:
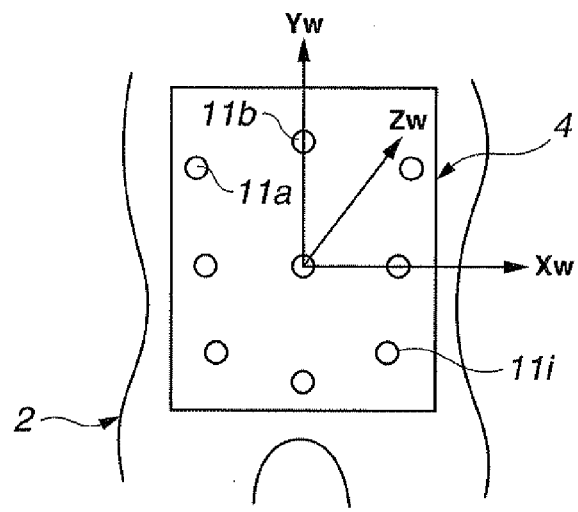
FIG. 3 is a diagram illustrating an example arrangement of a plurality of antennae included in an antenna unit and a coordinate system set for one of the antennae.
Figure 4A:
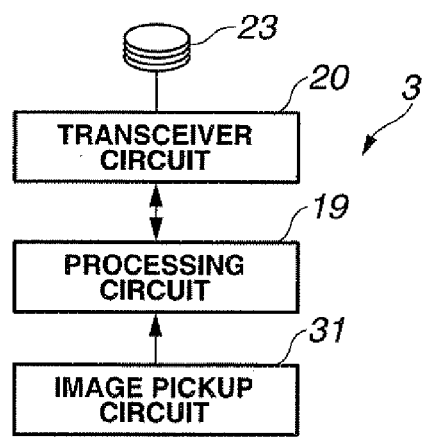
FIG. 4A is a diagram illustrating a schematic configuration of an electric system for transmission/reception of signals in a capsule-type endoscope.
Figure 4B:
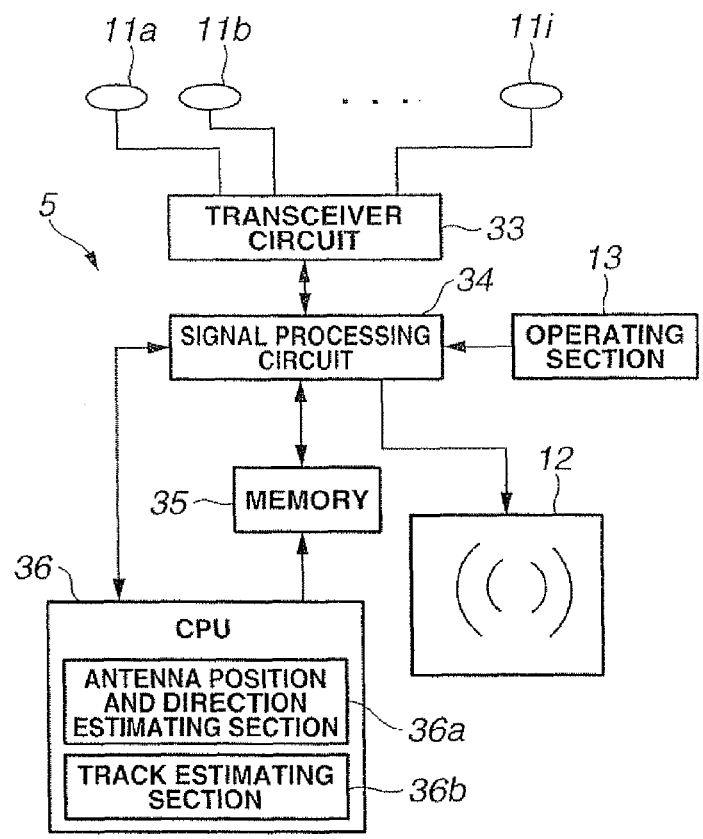
FIG. 4B is a diagram illustrating a schematic configuration of an electric system for transmission/reception of signals in an extracorporeal device.

FIGS. 1 to 12B relate to embodiment 1 of the present invention. FIG. 1A is a diagram illustrating the configuration of a capsule-type endoscopic device, etc., according to embodiment 1 of the present invention. FIG. 1B is a diagram illustrating a state in which an extracorporeal device in FIG. 1A is connected to a terminal apparatus. FIG. 2 is a diagram illustrating the inner configuration of the capsule-type endoscope. FIG. 3 is a diagram illustrating an example arrangement of a plurality of antennae included in an antenna unit and a coordinate system set for one of the antennae. FIG. 4A is a diagram illustrating a schematic configuration of an electric system for transmission/reception of signals in a capsule-type endoscope. FIG. 4B is a diagram illustrating a schematic configuration of an electric system for transmission/reception of signals in an extracorporeal device.

Figure 5A:
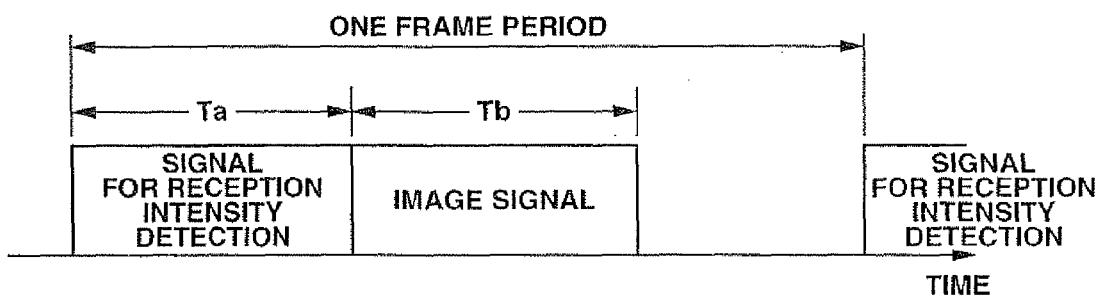
FIG. 5A is a diagram illustrating an example of an image signal, etc., sent wirelessly from a capsule-type endoscope.
Figure 5B:
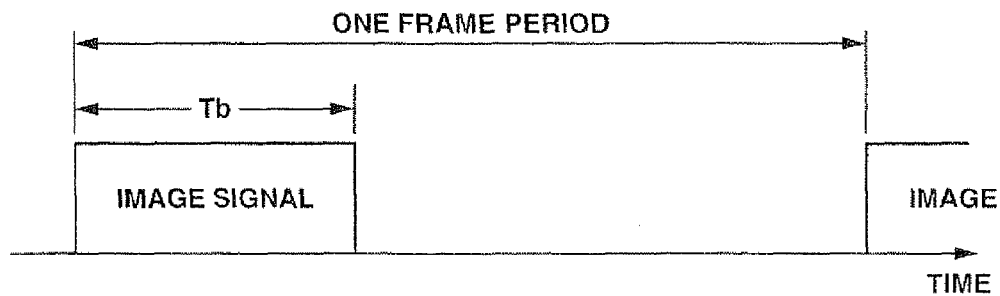
FIG. 5B is a diagram illustrating an example of an image signal, etc., sent wirelessly from a capsule-type endoscope, which is different from the example in FIG. 5A.
Figure 6A:
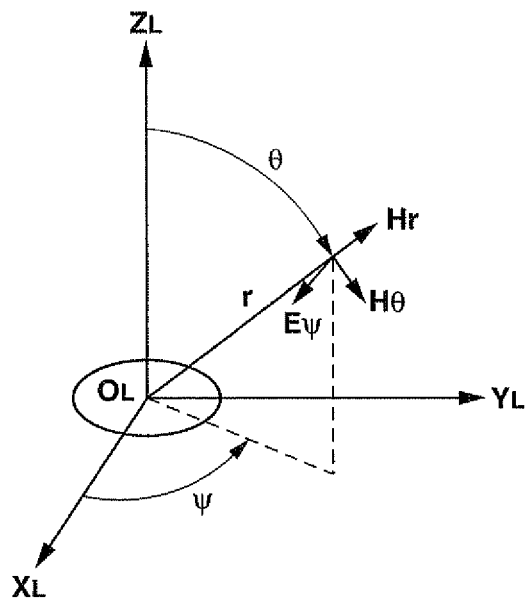
FIG. 6A is a diagram indicating, by means of polar coordinates, components of an electromagnetic field, etc., at a given position, which is sent from an antenna formed of an circular coil in a capsule-type endoscope.
Figure 6B:
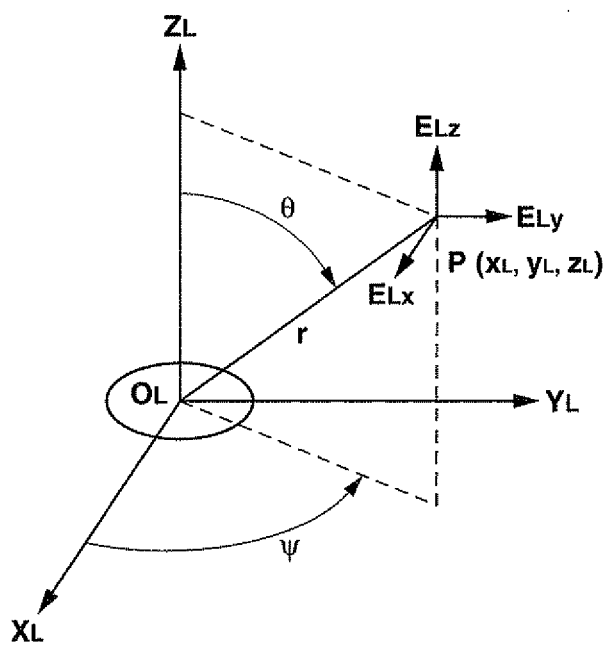
FIG. 6B is a diagram indicating, by means of orthogonal coordinates, components of an electromagnetic field, etc., at a given position, which is sent from an antenna formed of a circular coil in a capsule-type endoscope.
Figure 7:
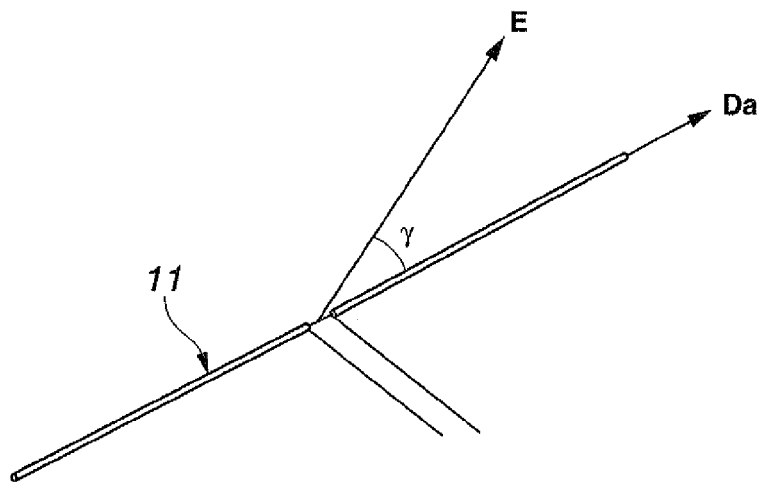
FIG. 7 is a diagram illustrating an electromotive force detected when an electric field generated by the antenna in FIG. 6 is received by a rod-like antenna in an antenna unit.

Also, FIG. 5A is a diagram illustrating an example of an image signal, etc., sent wirelessly from the capsule-type endoscope. FIG. 5B is a diagram illustrating an example of an image signal, etc., sent wirelessly from a capsule-type endoscope, which is different from the example in FIG. 5A. FIG. 6A is a diagram indicating, by means of polar coordinates, components of an electromagnetic field, etc., at a given position, which is sent from an antenna formed of an circular coil in a capsule-type endoscope. FIG. 6B is a diagram indicating, by means of orthogonal coordinates, components of an electromagnetic field, etc., at a given position, which is sent from an antenna formed of a circular coil in a capsule-type endoscope. FIG. 7 is a diagram illustrating the relationship with a direction Da of a rod-like antenna included in the antenna unit that receives an electric field generated by the antenna shown in FIG. 6.

Figure 8:
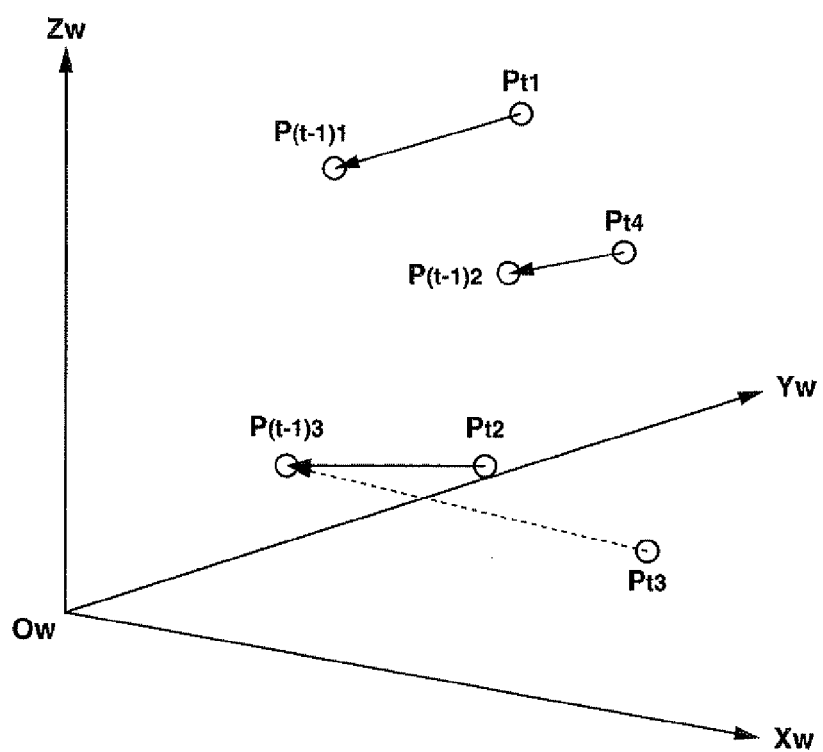
FIG. 8 is a diagram illustrating positions estimated at temporally adjacent times.
Figure 9:
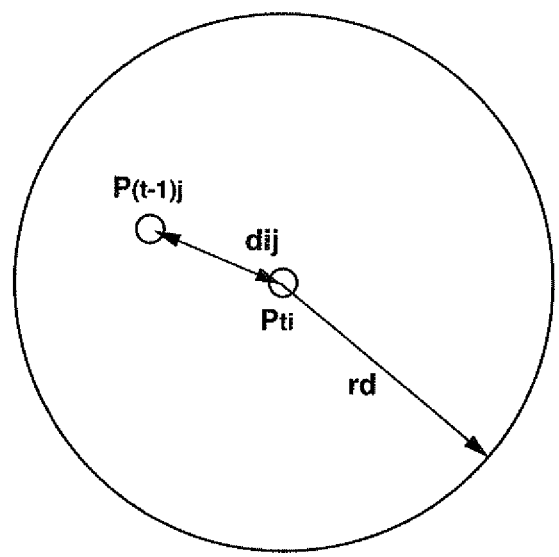
FIG. 9 is a diagram illustrating whether or not positions estimated at an adjacent time are within a sphere with a radius r set in advance.
Figure 10:
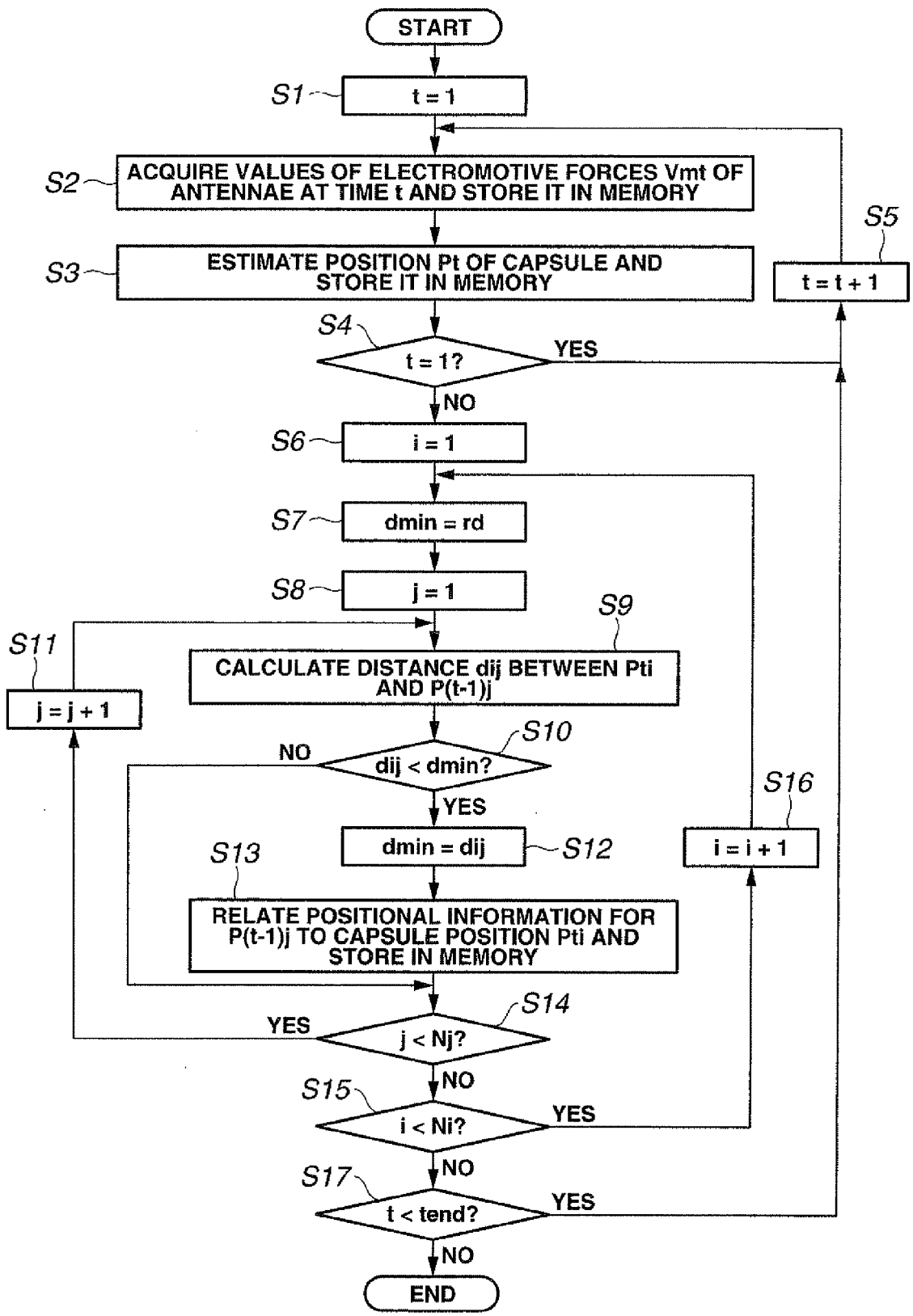
FIG. 10 is a flowchart of processing for determining connection relations, which are candidates for a route constituting a track, from positions estimated at adjacent times.
Figure 11:
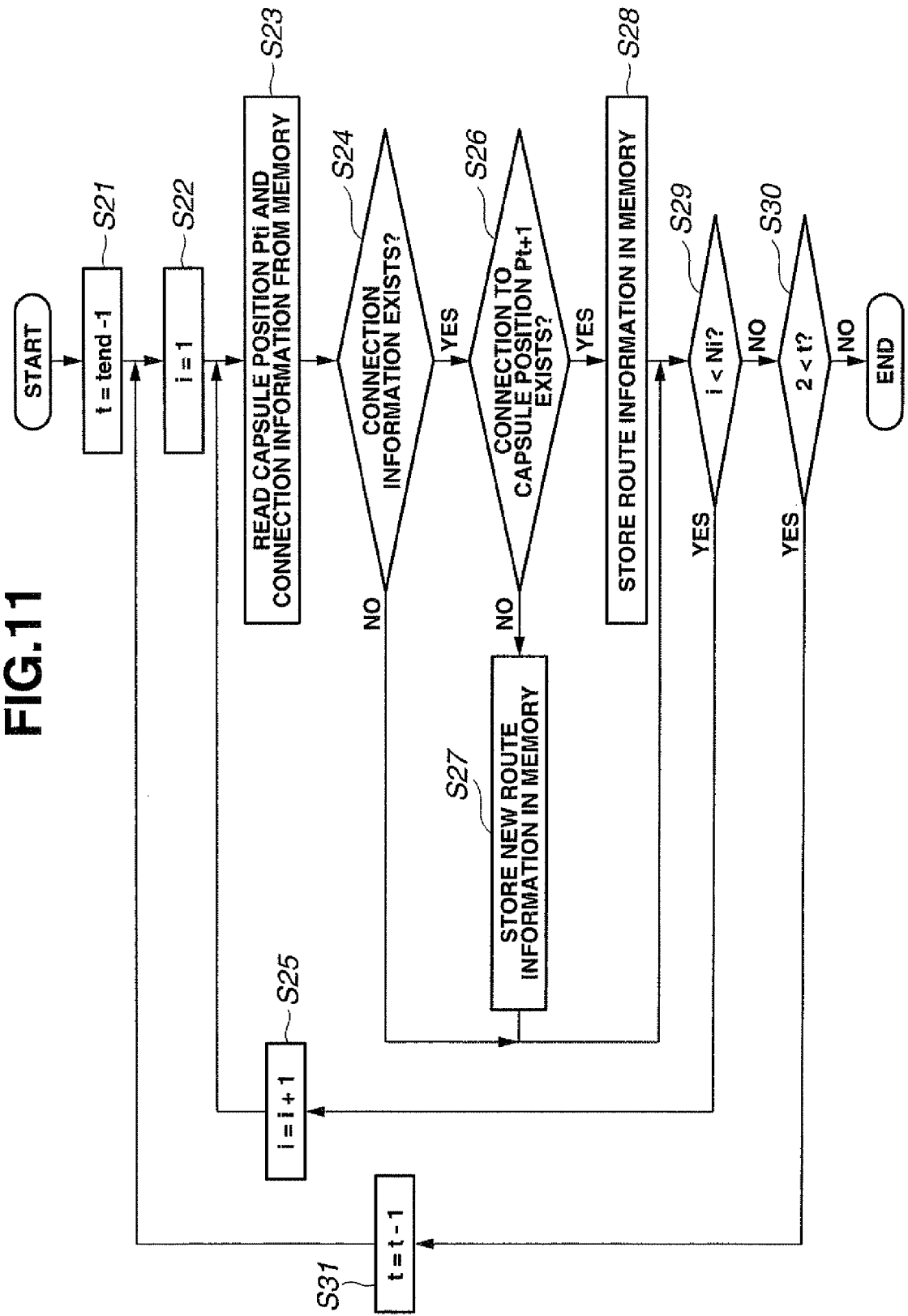
FIG. 11 is a flowchart illustrating the content of processing for calculating a track after the processing in FIG. 10.
Figure 12A:
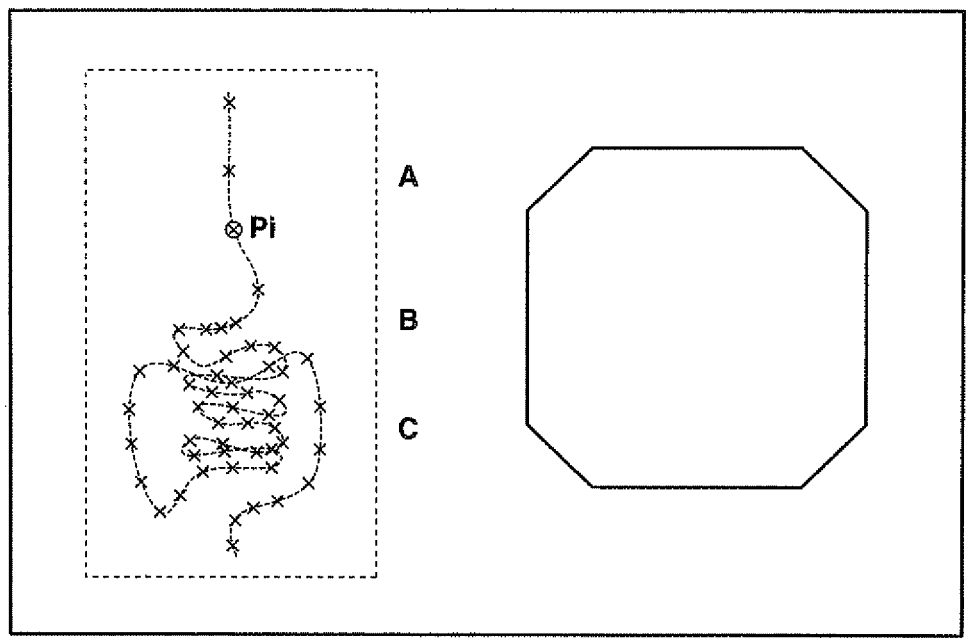
FIG. 12A is a diagram illustrating an example of a state of display where an image picked up by a capsule-type endoscope and positions forming a calculated track are both displayed.
Figure 12B:
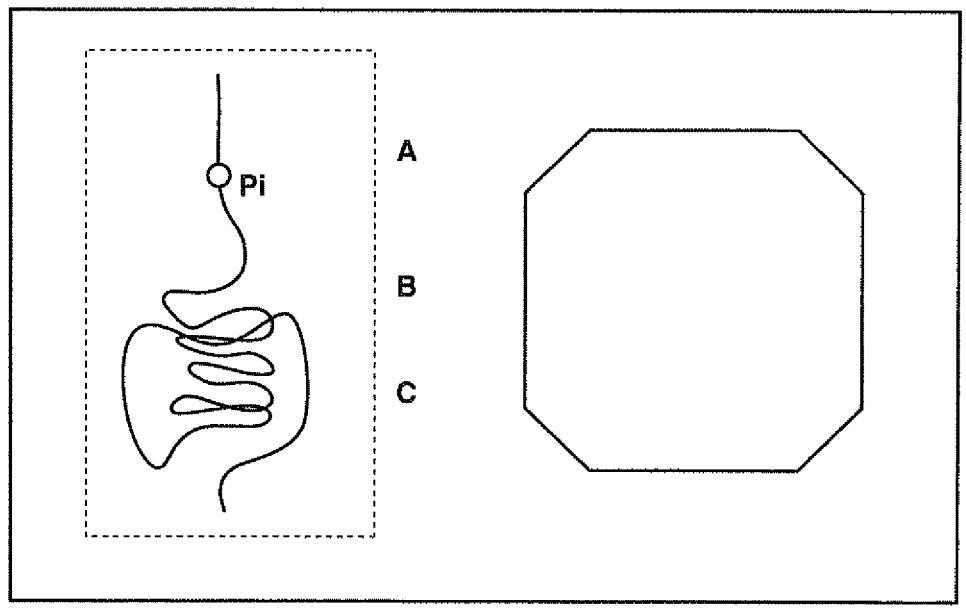
FIG. 12B is an example of a state of display where an image picked up by a capsule-type endoscope and positions forming a calculated track are both displayed, which is different from the example in FIG. 12A.

Also, FIG. 8 is a diagram illustrating multiple positions estimated at temporally adjacent times. FIG. 9 is a diagram illustrating whether or not positions estimated at an adjacent time are within a sphere with a radius $r_d$ of a value set in advance. FIG. 10 is a diagram illustrating the content of processing for determining connection relations, which are candidates for a track, from positions estimated at adjacent times. FIG. 11 is a diagram illustrating the content of processing for calculating the track after the processing in FIG. 10. FIG. 12A is a diagram illustrating an example of a state of display where an image picked up by the capsule-type endoscope and the positions forming the calculated track are both displayed. FIG. 12B is a diagram illustrating an example of a state of display where an image picked up by the capsule-type endoscope and the positions forming the calculated track are both displayed, which is different from the example illustrated in FIG. 12A.

As shown in FIG. 1A, a capsule-type endoscopic device 1 according to embodiment 1 of the present invention includes: a capsule-type endoscope 3 that, e.g., picks up an image of the inside of a body cavity, as a capsule-type in-vivo device that is inserted into the body cavity by being swallowed by a patient 2 from the mouth; and an extracorporeal device (or an external device) 5 that is arranged outside the body of the patient 2 and connected to an antenna unit 4 that wirelessly receives information on an image picked up by the capsule-type endoscope 3, as its main components.

As shown in FIG. 1B, this extracorporeal device 5 is attached to a cradle 6 and thereby electrically connected to a terminal apparatus 7, which is a personal computer or the like. Also, the terminal apparatus 7 is capable of, e.g., loading an image stored in the extracorporeal device 5 in this terminal apparatus 7 via input and operating devices such as a keyboard 8a and/or a mouse 8b and displaying the loaded image on a monitor section 8c.

As shown in FIG. 1A, a jacket 10 worn by the patient 2, which is used when he/she swallows the capsule-type endoscope 3 to undergo an endoscopic examination, is provided with the antenna unit 4 equipped with a plurality of antennae 11.

Signals based on an image of a subject that is picked up by the capsule-type endoscope 3 and sent from an antenna 23 (see FIG. 2) incorporated therein, are received by the plurality of antennae 11 in the antenna unit 4. Consequently, the extracorporeal device 5 connected to the antenna unit 4 can store the image picked up by the capsule-type endoscope 3.

Also, this extracorporeal device 5 has the shape of, e.g., a box, and on its front surface, a liquid-crystal monitor 12 that displays images and an operating section 13 for, e.g., performing an operation to give instructions are provided.

The extracorporeal device 5 may be constructed to only have, e.g., a LED for displaying a warning relating to the remaining battery level, and a power supply switch as the operating section 13. Also, a portable display device (viewer), which is not shown, may be connected to the extracorporeal device 5 as a second extracorporeal device, the portable display device processing image signals sent from the capsule-type endoscope 3 and displaying an image on a liquid-crystal monitor equipped with the portable display device.

As shown in FIG. 2, the capsule-type endoscope 3 includes: an exterior member 14 having the shape of a cylinder with its rear end closed, and a dome-shaped cover 14a, which is rounded substantially in the shape of a hemisphere, connected by an adhesive to, and thereby closing, a distal end of this cylinder. Thus, the exterior of the capsule-type endoscope 3 has the shape of a capsule and a watertight construction in its entirety when the exterior member 14 and the cover member 14a are connected.

At a portion around the center of the cylinder in this transparent dome-shaped cover 14a, an objective lens 15 that forms an image entered via the dome-shaped cover 14a is arranged in the state of being attached to a lens frame 16. At the position where an image is formed by the objective lens 15, here, a CCD imager 17 is arranged as an image pickup device.

Also, around the objective lens 15, four white LEDs 18 are arranged on the same plane as an illumination system. Also, for example, on the back side of the CCD imager 17, a processing circuit 19 that drives the white LEDs 18 to emit light and drives the CCD imager 17 to perform signal processing for generating image signals from image pickup signals inputted from the CCD imager 17, a transceiver circuit 20 having a function that transmits image signals and receives signals from the extracorporeal device 5, and button-shaped batteries 21 that supply power to the processing circuit 19 and the transceiver circuit 20 are arranged inside the exterior member 14.

Also, at the rear end of the button-shaped batteries 21, that is, inside the other semispherical shape, an antenna 23 having the shape of a circular coil (circular loop coil), which is connected to the transceiver circuit 20 and sends/receives radio waves, is arranged. Also, the CCD imager 17, the white LEDs 18 and the respective circuits are provided on substrates, which are not shown, and the respective substrates are connected via flexible substrates.

The processing circuit 19 in the capsule-type endoscope 3 controls, by means of a control signal, the timing for the CCD imager 17 to pick up an image to make it pick up two frames of images per second in ordinary image pickup, and to make it pick up, e.g., 15 to 30 frames of image for a site where the capsule-type endoscope 3 moves at a relatively high speed like esophagus.

Also, the antenna 23 receives signals sent from the extracorporeal device 5. Then, the signals received by the antenna 23 are processed by the transceiver circuit 20 and then sent to the processing circuit 19. The processing circuit 19 controls, e.g., the image pickup timing for the CCD imager 17 and turning on/off of the white LEDs 18 based on the signals sent thereto. A circuit that can turn on/off the power in the capsule-type endoscope 3 by means of putting a magnetic body such as a magnet close thereto may be incorporated in the processing circuit 19 in the capsule-type endoscope 3 to acquire images by turning on the power of the capsule-type endoscope 3 before the patient swallows the capsule-type endoscope 3.

The antenna unit 4 equipped with the jacket 10 worn by the patient 2 shown in FIG. 1A includes antennae 11a, 11b, . . . , and 11i in close up, as shown in FIG. 3.

The transmission and reception portions of the capsule-type endoscope 3 and the extracorporeal device 5 are configured as shown in FIGS. 4A and 43. As shown in FIG. 4A, the capsule-type endoscope 3 processes signals based on an image of a subject picked up by an image pickup circuit 31 (including the white LEDs 18 and the CCD imager 17) at the processing circuit 19, modulates them to high frequency signals at the transceiver circuit 20, and then sends them in the form of radio waves from the antenna 23 formed of a circular loop coil.

The signals sent from the antenna 23 are received by the plurality of antennae 11a, 11b, . . . 11i included in the antenna unit 4 outside the body. Then, the signals are demodulated by a transceiver circuit 33 connected to the plurality of antennae 11a, 11b, . . . 11i, and inputted to a signal processing circuit 34, and then converted into image signals by this signal processing circuit 34, thereby an image of the subject being displayed on the liquid-crystal monitor 12 and image data corresponding to the image of the subject, etc., being stored in a memory 35.

Also, the image data stored in the memory 35 can be sent to the liquid-crystal monitor 12 by a user's instruction via the operating section 13. This enables the user to display images acquired in the past observations, etc., on the display surface of the liquid-crystal monitor 12.

Also, in the present embodiment, the extracorporeal device 5 is provided with an antenna position and direction estimating section 36a configured using, e.g., a CPU 36. This antenna position and direction estimating section 36a performs estimation processing for estimating the position and direction of the antenna 23 incorporated in the capsule-type endoscope 3 to calculate the position and direction of the antenna 23.

As described later, in this estimation processing, an arbitrary position and direction are set in the initial state and the processing for estimating a position and direction relative to them using the Gauss-Newton method is repeatedly performed. At that time, estimation is repeated by the estimation processing until the displacement from the value before the estimation becomes equal to or lower than a small value. In the words, the extracorporeal device 5 in the present embodiment includes: estimation means for perform estimation processing; and update and correction means for updating and correcting an estimation value estimated by the estimation means (specifically, position and direction) so that the difference value between the estimation value and the value before the estimation becomes equal to or lower than a predetermined value.

Also, upon an instruction signal for, e.g., changing the image pickup cycle being inputted to the signal processing circuit 34 as a result of the operating section 13 provided in the extracorporeal device 5 being operated, this signal processing circuit 34 sends the instruction signal to the transceiver circuit 33. Then, the transceiver circuit 33 modulates the instruction signal and send it from the antennae 11a, 11b, . . . 11i.

The instruction signal sent from the antennae 11a, 11b, . . . 11i is received by the antenna 23, and demodulated by the transceiver circuit 20. Then, the transceiver circuit 20 performs an operation to, e.g., change the image pickup cycle according to the demodulated instruction signal.

In the present embodiment, when a signal of an image picked up by the image pickup circuit 31 is sent from the antenna 23 in the capsule-type endoscope 3 to the extracorporeal device 5, for example, as shown in FIG. 5A, a reception intensity detection signal that facilitates reception intensity detection is sent together with the image signal.

In other words, in each one frame period, a detection period Ta for sending a signal for reception intensity detection, and an image signal period Tb for sending an image signal are provided. Also, in the intensity detection period Ta, a signal for reception intensity detection with a certain intensity (amplitude) is sent.

Then, this signal for reception intensity detection is received by the antennae 11a, 11b, . . . 11i in the antenna unit 4 and then inputted to the transceiver circuit 33. The transceiver circuit 33 demodulates the signal for reception intensity detection and sends it to the signal processing circuit 34. The signal processing circuit 34 compares the signals for reception intensity detection received by the antennae 11s (s=a, b, . . . i) with one another, selects an antenna suitable for receiving the image signal sent by the capsule-type endoscope 3 based on the result of the comparison and receives the image signal. As shown in FIG. 5B, similar comparison processing may be performed omitting the signal for reception intensity detection and using the image signal only.

Also, the signal processing circuit 34 sends the image signal obtained via the antenna suitable for reception and the signals for reception intensity detection of the antennae 11s to the nonvolatile memory 35, such as a CompactFlash (registered trademark), connected to the signal processing circuit 34 to store the signals in the memory 35.

In this case, multiple, for example, two antennae may be selected as antennae for receiving the image signal to record two sets of image signals with the same content at the same time. Furthermore, at that time, the signal processing circuit 34 may sum up the intensities of image signals to be recorded in an amount corresponding to one frame, and leave one with the larger summation result in the memory 35 and delete the other.

Also, the signal processing circuit 34 sends the image signal obtained via the antenna that is most suitable for reception to the liquid-crystal monitor 12 connected to the signal processing circuit 34 to display an image of a subject picked up by the capsule-type endoscope 3.

In the present embodiment, as described above, the extracorporeal device 5 is provided with, e.g., the antenna position and direction estimating section 36a configured by the CPU 36. This antenna position and direction estimating section 36a calculates the position and direction of the antenna 23 incorporated in the capsule-type endoscope 3.

Also, in the present embodiment, the CPU 36 also functions as a track estimating section (track calculating section) 36b that recognizes the respective positions of the antenna 23 obtained chronologically (temporally), which have been calculated by the processing function of the antenna position and direction estimating section 36a, as the positions of the capsule-type endoscope 3, determines whether or not the respective positions meet the condition that the distances between the respective positions and their respective adjacent positions are equal to or lower than a predetermined value, and calculates a more accurate track (route) using those meeting the condition.

This antenna position and direction estimating section 36a, as described later, sets an initial value for the position and direction of the antenna 23 in the initial state (for example, the center position of the measurement space and any of X, Y and Z-axis directions).

Then, the CPU 36 estimates the detection value of a magnetic field generated at the extracorporeal antennae 11a, 11b, . . . 11i using the zeroth update value, and calculates an amount of update for the zeroth position and direction, from a square sum of the difference between the estimated detection value and the detection value actually detected (measured). Furthermore, the CPU 36 calculates the first position and/or direction from the zeroth position and direction and the update value from the zeroth position and direction.

The CPU 36 repeatedly performs similar estimation processing on this first position and/or direction and performs estimation value correction processing for determining an update value in which a change in the update value before and after the estimation has become equal to or lower than a sufficiently small value, as a position and direction for the antenna 23. The CPU 36 calculates the positions and directions with high accuracy in this manner. The information on the positions and directions calculated by the CPU 36 is stored in, e.g., the memory 35.

Next, a method for estimating a position and direction of the capsule-type endoscope 3 from a reception intensity signal detected using the plurality of antennae 11a, 11b, . . . 11i in antenna unit 4 in the present embodiment will be described.

As shown in FIG. 6A, in a coordinate system $X_L Y_L Z_L$ based on the antenna 23 formed of a circular coil or a circular loop arranged in the capsule-type endoscope 3, an electromagnetic field (electrostatic field, radiation electromagnetic field and induction electromagnetic field components) $H_r$, $H_\theta$ and $E_\phi$ at a given position P $(x_L, y_L, z_L)$ can be expressed by the following expressions.

$$H_r = (IS/2\pi)(jk/r^2 + 1/r^3)\exp(-jkr)\cos\theta$$

$$H_\theta = (IS/4\pi)(-k^2/r + jk/r^2 + 1/r^3)\exp(-jkr)\sin\theta$$

$$E_\phi = -(j\omega\mu IS/4\pi)(jk/r + 1/r^2)\exp(-jkr)\sin\theta \quad (1)$$

Here, $H_r$ and $H_\theta$ represent magnetic field components, and $E_\phi$ represents an electric field component. Also, I and S represent current flowing in the antenna 23 and the area of the circular coil forming the antenna 23. Also, r represents the distance $r=(x^2+y^2+z^2)^{1/2}$ between the antenna 23 and the given position, and k represents $k=\omega(\epsilon\mu)^{1/2}$ ($\epsilon$ is permittivity and $\mu$ is permeability), and j represents an imaginary unit.

Where an electromagnetic field generated by the antenna 23 arranged in the capsule-type endoscope 3 has a high frequency and as shown in FIG. 1A, there is a sufficient distance between the capsule-type endoscope 3 and the antennae 11s attached to the body surface of the patient 2, the radiation electromagnetic field components becomes the largest in the electromagnetic field reaching the antennae 11s (accordingly, the electrostatic field and induction electromagnetic field components become smaller than the radiation electromagnetic field component, and thus, they can be ignored). Accordingly, formula (1) can be expressed by formula (2) below.

$$H_r = 0$$

$$H_\theta = (IS/4\pi)(-k^2/r)\exp(-jkr)\sin\theta$$

$$E_\phi = (j\omega\mu IS/4\pi)(jk/r)\exp(-jkr)\sin\theta \quad (2)$$

Where the antennae 11s attached to the body surface of the patient 2 are antennae for detecting an electric field, the expression in formula (2) that is necessary for the detection is the electric field $E_\phi$.

The electric field $E_\phi$ in formula (2) represents a radiation electric field, which can be considered as a result based on alternating current phenomena. Accordingly, the instantaneous value of the electric field $E_\phi$ can be obtained by both sides of the expression (2) for the electric field $E_\phi$ being multiplied by $\exp(j\omega t)$ to extract the real part.

$$E_\phi \exp(j\omega t) = -(j\omega\mu IS/4\pi)(jk/r)\exp(-jkr)\sin\theta\exp(j\omega t) \quad (3)$$
$$= (\omega\mu ISk/4\pi r)(\cos U + j\sin U)\sin\theta$$

provided that $U=\omega t - kr$.

Here, when the real part in expression (3) is extracted, the instantaneous value of the electric field $E'_\phi$ can be expressed as follows.

$$E'_\phi = (\omega\mu ISk/4\pi r)\cos U \sin\theta \quad (4)$$

Also, when formula (4) is converted from a polar coordinate system $(r, \theta, \phi)$ to an orthogonal coordinate system $(X_L, Y_L, Z_L)$ as shown in FIG. 6B, the electric field components $E_{Lx}$, $E_{Ly}$ and $E_{Lz}$ of $X_L, Y_L, Z_L$ can be expressed as follows.

$$E_{Lx} = E'_\phi \sin\phi = (\omega\mu ISk/4\pi r^2)\cos U \cdot (-y_L)$$

$$E_{Ly} = E'_\phi \cos\phi = (\omega\mu ISk/4\pi r^2)\cos U \cdot x_L$$

$$E_{Lz} = 0 \quad (5)$$

Also, in the coordinate system $X_L, Y_L, Z_L$ based on the antenna 23 in the capsule-type endoscope 3, an expression for converting the position P $(x_L, y_L, z_L)$ into a coordinate system $X_W Y_W Z_W$ based on the body of the patient 2 can be expressed as follows:

$$\begin{pmatrix} X_{Lp} \\ Y_{Lp} \\ Z_{Lp} \end{pmatrix} = R^{-1} \left[ \begin{pmatrix} X_{Wp} \\ Y_{Wp} \\ Z_{Wp} \end{pmatrix} - \begin{pmatrix} X_{WG} \\ Y_{WG} \\ Z_{WG} \end{pmatrix} \right] \quad (6)$$

$$= \begin{pmatrix} R_{00} & R_{10} & R_{20} \\ R_{01} & R_{11} & R_{21} \\ R_{02} & R_{12} & R_{22} \end{pmatrix} \left[ \begin{pmatrix} X_{Wp} \\ Y_{Wp} \\ Z_{Wp} \end{pmatrix} - \begin{pmatrix} X_{WG} \\ Y_{WG} \\ Z_{WG} \end{pmatrix} \right]$$

provided that $(x_{WP}, y_{WP}, z_{WP})$ and $(x_{WG}, y_{WG}, z_{WG})$ represent the position P and the position of the antenna 23 in the coordinate system $X_W Y_W Z_W$, respectively. Also, R, which is used in the first term on the right side of expression (6), represents a rotation matrix between the coordinate system $X_W Y_W Z_W$ and the coordinate system $X_L Y_L Z_L$, and can be calculated by the following expression.

$$\begin{pmatrix} R_{00} & R_{01} & R_{02} \\ R_{10} & R_{11} & R_{12} \\ R_{20} & R_{21} & R_{22} \end{pmatrix} = \begin{pmatrix} \cos\alpha\cos\beta & -\sin\alpha & \cos\alpha\sin\beta \\ \sin\alpha\cos\beta & \cos\alpha & \sin\alpha\sin\beta \\ -\sin\beta & 0 & \cos\beta \end{pmatrix}, \quad (7)$$

provided $\alpha$ and $\beta$ represent the rotation amount of the polar coordinate system.

Accordingly, an electric field $E_W$ at the certain position P $(x_{WP}, y_{WP}, z_{WP})$ in the coordinate system $X_W Y_W Z_W$ based on the body of the patient 2 can be expressed as $$\begin{pmatrix} E_{Wx} \\ E_{Wy} \\ E_{Wz} \end{pmatrix} = R \begin{pmatrix} E_{Lx} \\ E_{Ly} \\ E_{Lz} \end{pmatrix} = \begin{pmatrix} R_{00} & R_{01} & R_{02} \\ R_{10} & R_{11} & R_{12} \\ R_{20} & R_{21} & R_{22} \end{pmatrix} \begin{pmatrix} E_{Lx} \\ E_{Ly} \\ E_{Lz} \end{pmatrix}, \quad (8)$$

and expression (9) for the electric field $E_W$ below can be obtained by assigning expressions (5), (6) and (7) to expression (8).

$$\begin{pmatrix} E_{Wx} \\ E_{Wy} \\ E_{Wz} \end{pmatrix} = \frac{k_1}{r^2} \begin{pmatrix} 0 & (z_{Wp} - z_{WG}) & -(y_{Wp} - y_{WG}) \\ -(z_{Wp} - z_{WG}) & 0 & (x_{Wp} - x_{WG}) \\ (y_{Wp} - y_{WG}) & -(x_{Wp} - x_{WG}) & 0 \end{pmatrix} \begin{pmatrix} g_x \\ g_y \\ g_z \end{pmatrix}, \quad (9)$$

provided that $k_1$ is a constant, and $(g_x, g_y, g_z)$ represents the direction of the antenna 23.

An electromotive force Va detected when the electric field $E_W$ generated by the antenna 23 is received by, e.g., an antenna 11a included in the antenna unit 4, which is, e.g., a rod-like antenna as shown in FIG. 7, that is, a dipole antenna, can be calculated by the following expression.

$$Va = k_2 E_W \cos\gamma = k_2 (E_{Wx} D_{xa} + E_{Wy} D_{ya} + E_{Wz} D_{za}) \quad (10)$$

provided that $k_2$ represents a constant, and Da (see FIG. 7) represents the direction $(D_{xa}, D_{ya}, D_{za})$ of the antenna 11a in the antenna unit 4 in the coordinate system based on the patient.

Then, the CPU 36 calculates the position and direction of the antenna 23 based on the arrangement of the antennae 11s in the antenna unit 4, which are arranged on the body of the patient 2, the arrangement being, e.g., one illustrated in FIG. 3, by means of iterative refinement (using the Gauss-Newton method).

Here, it is assumed that x is a parameter for the position $(x_{WG}, y_{WG}, z_{WG})$ and direction $(g_x, g_y, g_z)$ of the antenna 23 and an initial value for the parameter is $x^{(0)}$.

Here, where the k-th order estimation value $x^{(k)}$ has been obtained by iterative refinement, and a model function V(x) for the electromotive force generated at the coils of the antennae 11s is expanded around $x^{(k)}$ using Taylor expansion, the first-order approximation can be expressed as follows.

$$V(x) = V(x^{(k)}) + \left[\frac{\delta V(x)}{\delta x}\right]_{x=x^{(k)}} (x - x^{(k)}) \quad (11)$$

At this time, where Vm is the electromotive force measured by the coils of the antennae 11s, the observation equation can be represented by $$Vm \cong V(x^{(k)}) + \left[\frac{\delta V(x)}{\delta x}\right]_{x=x^{(k)}} (x - x^{(k)}) \text{ with error } \sigma \text{ included} \quad (12)$$

Here, the approximately equal sign includes an error $\sigma$.

Also, movement of the first term on the right side of equality (11) to the left side results in:

$$\Delta Vm^{(k)} \cong A^{(k)} \Delta x^{(k)} \text{ with error } \sigma \text{ included} \quad (13),$$

provided that, $$\Delta Vm^{(k)} = Vm - V(x^{(k)}) = Vm - Vm^{(k)} \quad (14)$$

$$\Delta x^{(k)} = x - x^{(k)} \quad (15)$$

$$A_{js} = [\partial V_j(x)/\partial x_s]_{x=x^{(k)}} (j=1\sim n, s=a\sim i) \quad (16)$$

(the number of rows is an unknown number n, and the number of columns is the number i of coils for the antennae 11s). The solution $\Delta x^{(k)}$ can be expressed based on expression (15) as follows:

$$\Delta x^{(k)} = (A^{t(k)} W A^{(k)})^{-1} A^{t(k)} W \Delta Vm^{(k)} \quad (17)$$

provided that $A^t$ is a transposed matrix for A and W is a weighting matrix.

Accordingly, the estimation value of the parameter refined according to expression (14) can be obtained by $$x^{(k+1)} = x^{(k)} + \Delta x^{(k)} \quad (18)$$

As shown in FIG. 3, where nine antennae 11a, 11b, ... 11i are provided to a patient, the matrix A can be expressed by $$A = \begin{bmatrix} \frac{\delta V_a}{x_{wg}} & \frac{\delta V_a}{y_{wg}} & \frac{\delta V_a}{z_{wg}} & \frac{\delta V_a}{g_x} & \frac{\delta V_a}{g_y} & \frac{\delta V_a}{g_z} \\ \frac{\delta V_b}{x_{wg}} & \frac{\delta V_b}{y_{wg}} & \frac{\delta V_b}{z_{wg}} & \frac{\delta V_b}{g_x} & \frac{\delta V_b}{g_g} & \frac{\delta V_b}{g_z} \\ \vdots & \vdots & \vdots & \vdots & \vdots & \vdots \\ \frac{\delta V_i}{x_{wg}} & \frac{\delta V_i}{y_{wg}} & \frac{\delta V_i}{z_{wg}} & \frac{\delta V_i}{g_x} & \frac{\delta V_i}{g_g} & \frac{\delta V_i}{g_z} \end{bmatrix}, \quad (19)$$

and the weighting matrix W can be expressed by $$W = \begin{bmatrix} \sigma_0^2 & 0 & 0 & \cdots & 0 \\ 0 & \sigma_1^2 & 0 & \cdots & 0 \\ 0 & 0 & \sigma_2^2 & \cdots & 0 \\ \vdots & \vdots & \vdots & \ddots & \vdots \\ 0 & 0 & 0 & \cdots & \sigma_8^2 \end{bmatrix}, \quad (20)$$

provided that $\sigma_j$ (j=0, 1, . . . , 8) in the weighting matrix W is fluctuation amounts of measured voltages of the antennae 11j, such as environmental noise, for example.

Also, since the k-th ΔVm can be expressed by $$\Delta Vm = \begin{bmatrix} Vm_a - V_a(x^{(k)}) \\ Vm_b - V_b(x^{(k)}) \\ Vm_c - V_c(x^{(k)}) \\ \vdots \\ Vm_i - V_i(x^{(k)}) \end{bmatrix}, \quad (21)$$

and accordingly, a position and direction of the antenna 23 in the capsule-type endoscope 3 can be calculated by steps (a) to (d) below.

(a) Assume that k=0 and the initial value of the antenna 23 is a position $(x_{Wg}^{(0)}, y_{Wg}^{(0)}, z_{Wg}^{(0)})$ and a direction $(g_x^{(0)}, g_y^{(0)}, g_z^{(0)})$ (for example, the center position of the space in which the antenna 23 is measured, and the Z-axis vector (0, 0, 1));

(b) Calculate the k-th matrix using expressions (9), (20) and (21);

(c) Calculate the k-th update amount $\Delta x^{(k)}$ using expression (18); and (d) Repeat steps (b) to (d) until the update amount $\Delta x^{(k)}$ becomes small.

The estimation processing as described above enables highly-accurate position and direction estimation (calculation).

Also, in the present embodiment, as described below, even when multiple positions are estimated, a highly-accurate or highly-reliable track can be calculated by performing track estimation processing on the chronologically estimated and calculated positions at the track estimating section 36b.

In the aforementioned position and direction estimation steps, multiple positions of the antenna 23 or the capsule-type endoscope 3 may be estimated depending on the number and arrangement position of antennae 11 for reception, the manner to provide the position $(x_{Wg}, y_{Wg}, z_{Wg})^{(0)}$ at the initial value for the antenna 23, and noise, etc. The antenna 23 is secured in the capsule-type endoscope 3, and thus, if the position of the antenna 23 is estimated, the position of the capsule-type endoscope 3 is also determined.

Since the capsule-type endoscope 3 make relative small movements in a body cavity and picks up images at short intervals, the position estimated at a certain time and the position estimated at a time immediately before or after the certain time can be considered to be positions that are substantially the same or close to each other.

Accordingly, when the positions meeting the condition of adjacency are extracted from the multiple positions estimated at the time immediately before or after the certain time to obtain the connection relations between the positions estimated at the respective times, and the smallest route is calculated from the routes of the overall connection relations, the final track and the correct positions of the capsule-type endoscope 3 at the respective times can be calculated.

As shown in FIG. 8, it is assumed that the positions estimated at a time t−1 are P(t−1)1, P(t−1)2, . . . , and the positions estimated at a time t are Pt1, Pt2, . . . .

At this time, for the positions Pti (i=1, 2, 3, . . . ) estimated at the time t, the CPU 36, as shown in FIG. 9, sets a sphere with a radius $r_d$ whose value has been set in advance, corresponding to the distance that the capsule-type endoscope 3 can move during the time between position estimations of the capsule-type endoscope 3.

Then, the CPU 36 detects the estimated positions P(t−1)j (j=1, 2, 3, . . . ) at the time t−1, which are present in the sphere. Also, the CPU 36 calculates the distances dij between the positions Pti estimated at the time t and the detected estimated positions P(t−1)j at the time t−1, and then calculates the estimated positions P(t−1)j at the time t−1 providing the smallest distances dij.

The CPU 36 calculates the estimated positions at the time t−1 that are the closest to the respective estimated positions Pti (i=1, 2, 3, . . . ) at the time t, and stores such connection relations. For example, the CPU 36 relates information on addresses at which the estimated positions at the time t−1 is stored thereto to store as connection information.

In FIG. 8, the estimated position at the time t−1 that is the closest to the estimated position Pt3 is P(t−1)3. However, the distance between these two points is larger than $r_d$, the CPU 36 determines that the estimated position at the time t−1 connected to the estimation position Pt3 is one resulting from noise, etc., and does not store it as information to be used for a connection relation for the estimated position Pt3.

As described above, the CPU 36 performs position estimation for all the recorded data to obtain the connection relations. Then, the CPU 36 sets the estimated positions stored at the last as the starting points and the estimated positions stored at the first as the endpoints to search for the routes of the connection relations from the starting points and the endpoints using the connection information stored together with the respective estimated positions. Then, the CPU 36 calculates the smallest one of the obtained routes as a track, and determines the estimated positions at the respective times from the track.

As a modification, the CPU 36 may calculate the route including the largest number of points (estimated positions), select the route as a track, and determine the estimated positions at the respective times from the track. In this case, where multiple routes including the largest number of points have been obtained, the CPU 36 may select one whose overall route length is the smallest as a track.

Next, a track estimation operation will be described. As processing prior to track estimation, the CPU 36 performs processing for calculating (determining) whether or not two adjacent positions are positions in the connection relation meeting the condition for forming a track. The processing for calculating this connection relation will be described with reference to FIG. 10. FIG. 10 shows the content including an image pickup operation in a chronological manner.

Upon the processing for calculating the connection relation being started, as shown in step S1 in FIG. 10, the CPU 36 in the extracorporeal device 5 sets a time t to an initial value of 1, that is, t=1. In this way, the description with reference to FIGS. 10 and 11 shall be given in a simplified manner using a parameter obtained by making the time t to an integer.

Then, the CPU 36, as shown in step S2 in FIG. 10, acquires an electromotive force Vmt (which expresses that it is a value of the aforementioned electromotive force Vm at the time t) obtained at the time t via the antennae 11 on the extracorporeal device 5 side, and stores the value of the electromotive force Vmt in the memory 35, which is storing means.

Also, as shown in step S3 in FIG. 10, the CPU 36 estimates a position Pti of the capsule-type endoscope 3 at the time t using the value of electromotive force Vmt (acquired via the plurality of antennae 11 at the time t) stored in the memory 35, and stores the position Pti in the memory 35.

As described below, there is a case where multiple positions Pti at the time t are estimated, and in that case, the multiple positions Pti are stored in the memory 35. Also, in general, the number of positions Pti obtained varies if the time t varies. Accordingly, it is assumed that the number of positions obtained at the time t is Ni, and the number of positions obtained at a time t−1 is Nj.

Then, at the next step S4, the CPU 36 determines whether or not the parameter value for the time t is the initial value of 1.

In this case, since the parameter value for the time t is 1, the CPU 36 proceeds to step S5, and the parameter value is incremented by one, and then the processing at steps S1 and S2 is performed, and the CPU 36 proceeds to step S6 as a result of the determination at step S4. Then, in the processing at step S6 onward, processing for connecting the positions Pti estimated (calculated) at the time t, which include those affected by noise, to positions P(t−1)j estimated at a time t−1 one time before the time t as routes is performed.

At step S6, for the entire positions Pt estimated at the time t, that is, Ni positions Pti (i=1 to Ni), a parameter i indicating those positions is set to an initial value of 1, that is, i=1.

Then, at the next step S7, as shown in FIG. 9, the CPU 36 sets a prescribed radius $r_d$ as a value for a minimum distance $d_{min}$. Furthermore, at the next step S5, the CPU 36 sets a parameter j indicating the respective positions P(t−1)j estimated at the time t−1, that is, Nj positions P(t−1) (j=1 to Nj) to an initial value of 1, that is, j=1.

Then, at the next step S9, the CPU 36 calculates the distance between the position Pti of the capsule-type endoscope 3 estimated at the time t and the position P(t−1)j estimated at the time t−1.

Furthermore, at the next step S10, the CPU 36 determines whether or not the calculated distance dij is shorter than the minimum distance dmin set in advance at step S7. Then, if the result of the determination does not meet the condition of dij<dmin, the CPU 36 determines if the parameter j is smaller than the number of positions P(t−1)j estimated at the time t−1 that is, Nj at step S14. If this condition is met, the CPU 36, as shown in step S11, increments the value of the parameter j by one and returns to step S9, and repeats similar processing. The positions not meeting the condition at step S10 are not used for the processing for calculating a track of the movement of the capsule-type endoscope 3, which can be understood from the following steps.

Meanwhile, if it has been determined that the condition at step S10 is met, the CPU 36, as shown in step S12, updates the value of the minimum distance dmin by the distance dij. Furthermore, at the next step S13, the CPU 36 relates positional information on the position P(t−1)j of the capsule-type endoscope 3 estimated at the time t−1 one time before the time t to the position Pti estimated at the time t, and stores the same in the memory 35 as connection information. Also, in FIG. 10 (also in FIG. 11, etc.), the capsule-type endoscope is abbreviated simply to "capsule".

At the next step S14, the CPU 36 determines if the parameter j is smaller than the number Nj of positions P(t−1)j estimated at the time t−1. Also, if the condition at step S14 in FIG. 10 is met, the CPU 36 increments the value of j by one via step S11, and retunes to step S9 to repeat the same processing.

Then, if this value of j corresponds to the number Nj, the CPU 36 proceeds to the next step S15 to determine if the parameter i is smaller than the number Ni of positions Pti estimated at the time t. Furthermore, if the condition at step S15 in FIG. 10 is met, the CPU 36 proceeds to step S16 to increment the value of i by one, and retunes to step S7 and then repeats the same processing.

Subsequently, if this value of i corresponds to the number Ni, the CPU 36 proceeds to step S17 to determine if the parameter t is smaller than a time tend measured at the last. Then, if the condition of this parameter t being smaller than tend is met, the CPU 36 retunes to step S5 to increment the value of t by one and returns to step S2, and then repeats similar processing.

As described above, if the time t corresponds to the last time tend, the CPU 36 terminates this processing, and as shown in FIG. 11, performs processing for searching for the positions meeting the connection relation (which have been determined in the processing shown in FIG. 10), that is, searching for a route (calculating a track) to calculate (estimate) a track.

Upon the start of the processing for route search shown in FIG. 11, the CPU 36, at the first step S21, sets the time t, which is the time for performing the processing, to tend−1, which is a time one time before the last time tend used in the processing shown in FIG. 10. Then, the CPU 36, at the next step S22, sets the parameter i indicating one of the positions Pti estimated at the time t to an initial value of 1.

In the next step S23, the CPU 36 reads the position Pti of the capsule-type endoscope 3 and its connection information from the memory 35. Then, at the next step S24, the CPU 36 determines whether or not connection information exists in the read information.

If no connection information exists, the CPU 36, at step S29, determines if the position parameter i is smaller than Ni. If this condition is met, the CPU 36, as shown in step S25, increments the position parameter i by one, and performs the processing at steps S23 and S24 for the parameter i+1. Also, if it has been determined as a result of step S24 that connection information exists, the CPU 36 proceeds to the processing at step S26.

At step S26, the CPU 36 determines whether or not there is any connection with a position Pt+1 of the capsule-type endoscope 3 at a time t+1 following the time t (in the case of the time t=tend−1, t+1 tend). Then, if there is no such connection, the CPU 36 proceeds to step S27. At step S27, the CPU 36 stores new route information (for example, route information to the effect that the connection is discontinued) in the memory 35 and then returns to the processing at step S23, via step S25 depending on the condition at step S29.

Meanwhile, if the CPU 36 has determined at step S26 that connection with a position Pt+1 of the capsule-type endoscope 3 at the following time t+1 exists, it proceeds to step S28. Then, in this case, at step S28, the CPU 36 stores information to the effect that they are connected, in the memory 35 as route information.

At the next step S29, the CPU 36 determines whether or not the position parameter i is smaller than Ni. Then, if the parameter i is smaller than Ni, the CPU 36 increments the value of the position parameter i by one via step S25, and then returns to the processing at step S22.

As described above, the CPU 36 repeats the processing at steps S22 to S29 while sequentially incrementing the value of the parameter i by one. Then, when the parameter i corresponds to Ni, the CPU 36 proceeds to step S30. At step S30, the CPU 36 determines whether or not the time t is equal to or lower than an initial value of 2.

If the time t is not equal to or lower than 2 (that is, not smaller than 3), the CPU 36, as shown in step S31, decrements the value of the time t by one, and then returns to the processing at step S22. Then, the CPU 36 sets the time t to the time t−1 one time before the time t and repeats similar processing. Thus, when the time t has the initial value of 2, the CPU 36 terminates this processing.

Through the processing at the aforementioned series of steps, routes from the positions Pti of the capsule-type endoscope 3 at the time t having the initial value of 1 to the positions Ptend of the capsule-type endoscope 3 at the last time tend are calculated.

Then, as described above, the CPU 36 calculates the shortest route, from among the routes from the starting point to the endpoint that have been obtained in such a manner as described above to determine it to be a track, and determines the estimated positions at the respective times from the track.

As a modification of the present embodiment, the CPU 36 may set the route obtained from the starting point to the end point that includes the largest number of estimated position, as a track. Also, if multiple routes including the largest number of points have been calculated based on, e.g., the preset value of the distance $r_d$, the CPU 36 may determine one whose entire length is the shortest to be a track. Also, in that case, the CPU 36 may determine the estimated positions at the respective times from the shortest route, that is, the track.

Alternatively, the CPU 36 may rank the routes according to the number of points included in the routes, and calculate the lengths of the entire routes only for the highly-ranked routes to determine the route whose entire length is the shortest as a track. Also, the CPU 36 may determine the estimated positions at the respective times from the track in that case.

Alternatively, the CPU 36 calculates the total sum of the cost values obtained when position estimation has been performed, for the routes highly ranked when the routes have been ranked according to the number of points included in the routes (e.g., the sums of the squares of the residual differences between the measured values and the calculated values) to determine the route whose total sum of the cost values is the smallest to be a track, and determines the estimated positions at the respective times from the track.

When one track has been calculated in such a manner as described above, the track is displayed on, e.g., the monitor section 8c shown in FIG. 1B.

FIGS. 12A and 12B show examples of display on the monitor section 8c. In FIG. 12A, on the left side of the display screen, a track of the movement of the capsule-type endoscope 3 in a body cavity is displayed by connecting the estimated positions of the capsule-type endoscope 3 in the body cavity with straight lines, and on the right side of this display screen, the image picked up at an estimated position Pti, which has been designated (via, e.g., a cursor on the left side), is displayed.

Also, signs A, B and C appearing on the right side of the track formed by the estimated positions on the left side of the display screen indicate the general positions of organs in the body cavity, and more specifically, sign A indicates the esophagus, sign B indicates the small intestine, and sign C indicates the large intestine.

Other than the display method shown in FIG. 12A, for example, display may also be provided as shown in FIG. 12B.

In this case, the display is provided by performing interpolation, such as spline interpolation, between the respective adjacent positions to connect the respective positions of the capsule-type endoscope 3 estimated for the respective frames with a smooth curve.

As described above, since the estimated positions in the body cavity and the corresponding picked up images can be displayed, it is possible to easily determine in which site in the body cavity the image was picked up, enabling efficient diagnosis.

Also, in the case where a possible lesion has been found from an obtained image and there has arisen a need for a closer endoscopic examination of the site, a re-examination or treatment, etc., can efficiently be conducted since the position can be estimated with high accuracy, enabling approaching the site smoothly in a short time.

The present embodiment provides the following advantageous effects.

Even when multiple positions of the capsule-type endoscope 3 have been estimated depending on the number of antennae included in the antenna unit 4, the arrangement position of the antennae included in the antenna unit 4, the manner to provide the position $(x_{Wg}, y_{Wg}, z_{Wg})^{(0)}$ of an initial value for an antenna 23, and noise, etc., the position of the capsule-type endoscope 3 can uniquely be determined by means of a proper method, enabling a track to be calculated.

Also, since a track is calculated by selecting positions meeting a predetermined condition, the calculated track and the respective positions in the track are highly reliable, and can effectively be utilized for diagnosis, etc.

Embodiment 2

Next, embodiment 2 of the present invention will be described with reference to FIGS. 13A to 15. The configuration of the present embodiment is similar to that of embodiment 1, and is different from that of embodiment 1 in the content of processing provided by the program in the track estimating section to estimate a track.

In the present embodiment, as described below, a living body in which the positions of the capsule-type endoscope 3 are estimated is divided into a plurality of regions to calculate the regions including the respective estimated positions of the capsule-type endoscope 3 in a chronological manner. Then, processing for calculating the routes from the starting point to the endpoint for the estimated positions to determine the route including the largest number of regions to be a track is performed.

Next, the operation of the present embodiment will be described with reference to FIG. 13A onward.

Figure 13A:
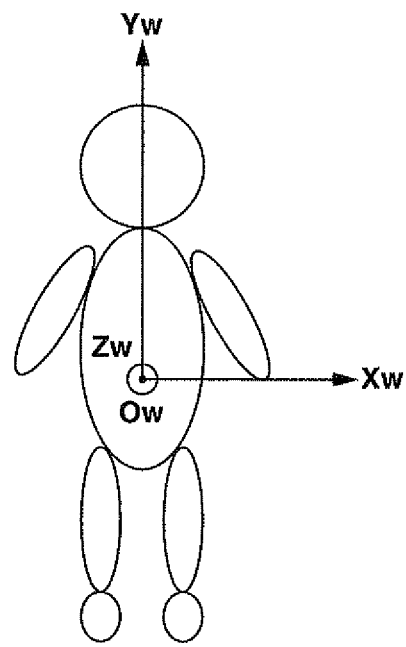
FIG. 13A is a diagram illustrating a coordinate system $X_w Y_w Z_w$ based on a human body.
Figure 13B:
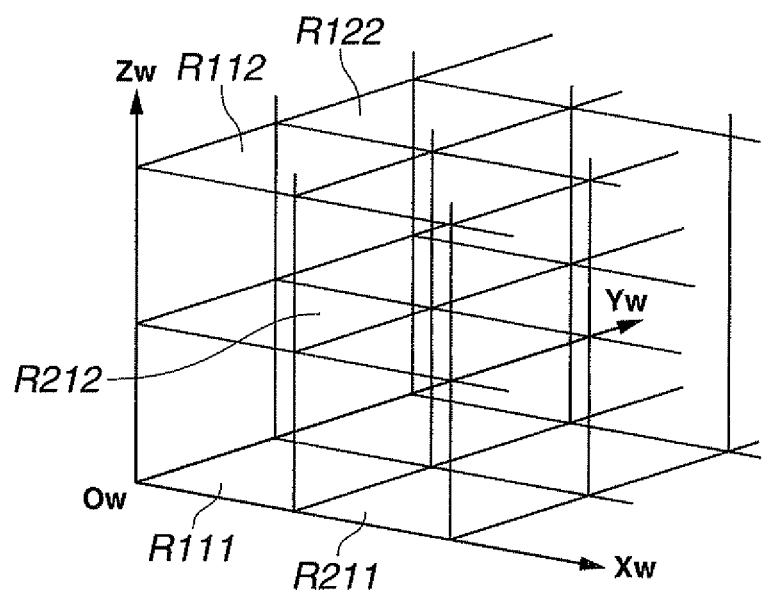
FIG. 13B is a diagram illustrating a state in which a space where a capsule-type endoscope 3 exists is divided into a plurality of regions.

FIG. 13A is a diagram illustrating a coordinate system $X_W Y_W Z_W$ based on a human body. FIG. 13B is a diagram illustrating a state in which a space where the capsule-type endoscope 3 exists is divided into a plurality of regions (x=1, 2, 3, ..., y=1, 2, 3, ..., and z=1, 2, 3, ...) (for example, cubes 2 cm on a side).

In embodiment 1, as shown in FIG. 9, the connections that meet the condition that the distance dij between positions Pti and P(t−1)j at adjacent times t and t−1 is equal to or shorter than a distance $r_d$ are extracted and used as connection information for determining routes or a track.

Meanwhile, in the present embodiment, in order to further increase the speed of arithmetic processing, or connections to be saved as connection information are further narrowed down. The CPU 36 divides a space where the capsule-type endoscope 3 exists into a plurality of regions $R_{xyz}$, and searches for regions $R_{xyz}$ including positions Pti estimated at a time t to determine the region including many estimated positions to be a connected region used for route search (or track estimation).

In this case, the positions Pti estimated at the time t are dispersed in multiple regions, the CPU 36 determines the region including the largest number of positions to be the connected region, and the positions included in the regions other than that region are not used for route search. As described above, even when there are a large number of estimated positions due to noise, etc., a track can be calculated in a short time by reducing the number of positions used for route search.

Also, the CPU 36 determines whether or not the regions $R_{xyz}$ including the positions Pti and P(t−1)j estimated at the times t and t−1 are connected regions from their positional relationship.

More specifically, if two regions including the positions Pti and P(t−1)j estimated at the times t and t−1 are not in the same region, the CPU 36 determines only regions that meet the relationship in which they are adjacent regions, in other words, regions meeting a particular region relationship in which they are close to each other within a small distance, to be regions connected by the movement of the capsule-type endoscope 3. Then, the CPU 36 does not determine the regions that are not in the relationship in which they are adjacent to each other, for example, the regions in the relationship in which they are remote from each other to be connected regions.

Figure 14:
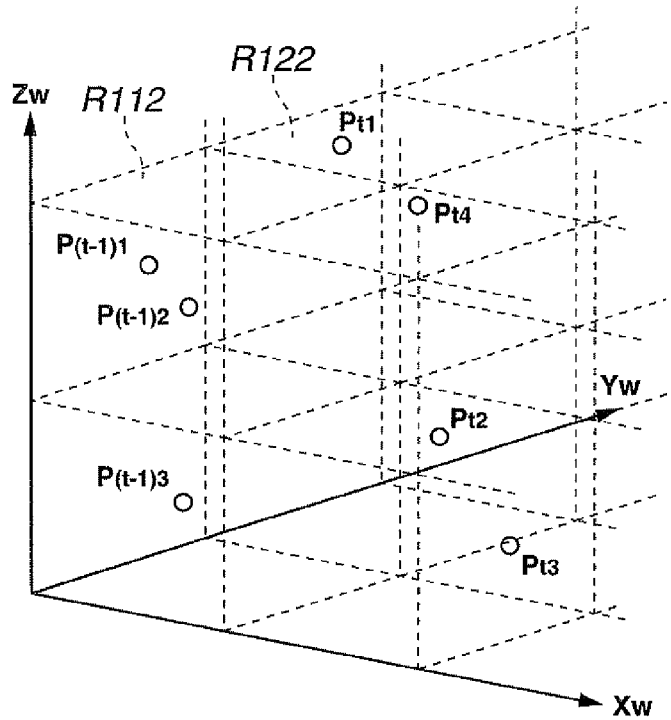
FIG. 14 is a diagram illustrating the relationship between positions estimated at adjacent times and small regions.

FIG. 14 is a diagram illustrating the respective positions P(t−1)j (j=1, 2, 3, . . . ) and Pti (i=1, 2, 3, . . . ) estimated as positions of the capsule-type endoscope 3 from multiple output values of the antennae 11 obtained at the times t−1 and t.

The CPU 36 in the extracorporeal device 5 calculates regions $R_{xyz}$ including the respective estimated positions Pti (i=1, 2, 3, . . . ).

In FIG. 14, the positions estimated at the time t are Pt1 to Pt4, and the positions estimated at the time t−1 are P(t−1)1 to P(t−1)3. In this case, the positions Pt1 and Pt4 are included in a region R122, the position Pt2 is included in a region R121, and the position Pt3 is included in a region 211. Also, the positions P(t−1)1 and P(t−1)2 are included in a region R112, and the position P(t−1)3 is included in a region R111.

Also, the CPU 36 determines whether or not each of the spatial relationships between the estimated positions at the times t−1 and t meets the connection relationship for connected regions to be saved as connection information. In this case, whether or not the regions are connected regions is determined depending on whether or not they are adjacent regions.

Then, the CPU 36 stores information on connected regions obtained from the regions obtained at the time t and the regions obtained at the time t−1, in the memory 35. Also, the CPU 36 records the extracted region and its connection information for all the stored data.

The CPU 36 sets the region stored at the last to be a starting point, and the region stored at the first to an endpoint, and performs processing similar to the track estimation processing described in embodiment 1, using the connection information stored together with the extracted regions to calculate the routes from the starting point to the endpoint.

The CPU 36 calculates the route including the largest number of regions, and determines the estimated positions at the respective times from the obtained route. The estimated positions in this case are the center positions (barycentric positions) of the regions.

In the specific example in FIG. 14, as described above, the largest number of positions, i.e., Pt1 and Pt4, are included in the region RI 22 at the time t and the largest number of positions, i.e., P(t−1)1 and P(t−1)2, are included in the region R112 adjacent to the region R122 at the time t−1.

These regions R122 and R112 are recognized as connected regions. The positions Pt2, Pt3 and P(t−1)3 included in the other regions are not used for route search.

Also, since these regions R122 and R112 are adjacent to each other, they are recognized as connected regions used for route search.

Figure 15:
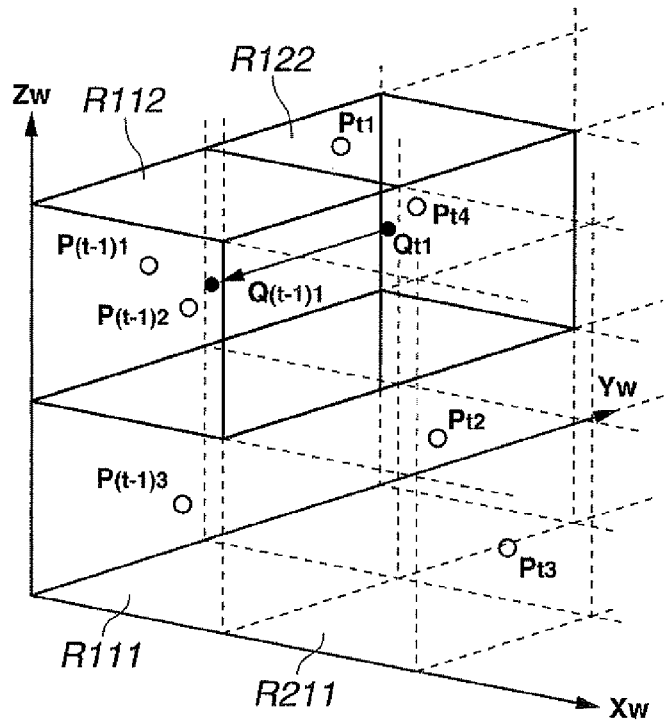
FIG. 15 is a diagram illustrating a manner in which connection relations that are candidates for calculating a track are determined from a plurality of positions estimated at adjacent times.

FIG. 15 illustrates a manner in which connected regions are specifically determined in the state shown in FIG. 14. In other words, FIG. 15 is a diagram illustrating a manner to determine the connection relations with the regions at the time t−1 from the regions obtained at the time t.

In FIG. 15, in the case of the connected regions R122 and R112 adjacent to each other, each having the largest number of estimated positions, the estimated position at the time t is the center position (barycenter position) Qt1 of the region R122, and the estimated position at the time t−1 is the center position (barycenter position) Q(t−1)1 of the region R112. In FIG. 15, these two connected regions R112 and R1122 are indicated with solid lines.

As described above, the CPU 36 searches for routes from the starting point to the endpoint and finally calculates one track.

Figure 16:
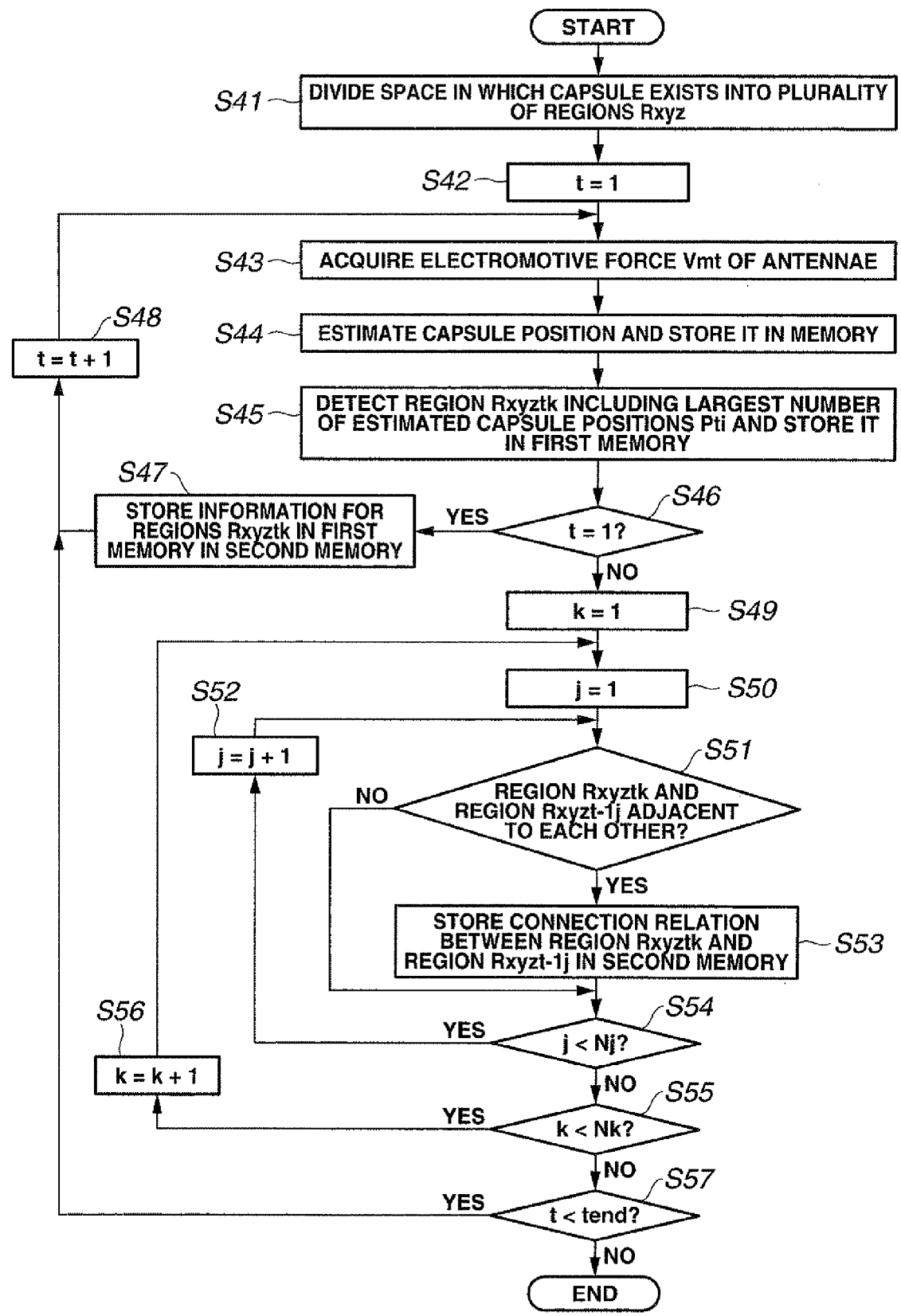
FIG. 16 is a flowchart of the content of processing for determining connection relations, which are candidates for calculating a track, from a plurality of positions estimated at adjacent times.

Next, processing for determining connection regions will be described with reference to FIG. 16. Upon the start of the operation, at the first step S41, the CPU 36 performs processing for dividing a space where the capsule-type endoscope exists into a plurality of regions $R_{xyz}$.

Then, at the next step S42, the CPU 36 sets the time t to an initial value of 1, and then, at the next step S43, acquires an electromotive force Vmt obtained at the time t via the antennae 11.

In the next step S44, the CPU 36 estimates the position Pti of the capsule-type endoscope 3 using the value of the electromotive force Vmt at the time t, and stores it in the memory 35. Since multiple positions Pti may exist, they are distinguished from one another by providing the subscript i thereto.

In the next step S45, the CPU 36 detects the region $R_{xyztk}$ including the largest number of estimated positions Pti of the capsule-type endoscope 3 and stores it in, e.g., a first memory in the memory 35. In this case, multiple regions $R_{xyztk}$ may exist. Here, the subscript t indicates a time, k indicates a parameter k (k=1, 2, . . . $N_k$) for distinguishing multiple regions $R_{xyzt}$ detected at the time t from one another.

In the next step S46, the CPU 36 determines whether or not the time t is its initial value, that is, t=1. Then, in the case of t=1, at step S47, the CPU 36 stores the information on the regions $R_{xyztk}$ stored in the first memory in the memory 35, in a second memory, and the next step S48, sets the time t to t+1, and then returns to step S43.

Then, the CPU 36 performs the processing at steps S43 to S46. In this case, the CPU 36 determines in the determination at step S46 that t is not 1, and proceeds to the processing at step S49.

At step S49, the CPU 36 sets the parameter k to its initial value, that is, k=1. Subsequently, at the next step S50, the CPU 36 further sets a parameter j to its initial value, that is, j=1.

Then, at the next step S51, the CPU 36 determines whether or not the region $R_{xyztk}$ and the region $R_{xyzt-1j}$ are adjacent to each other. Here, the region $R_{xyzt-1j}$ indicates a parameter j (j=1, 2, . . . $N_j$) for distinguishing, from one another multiple, the regions $R_{xyzt-1}$ estimated to include the largest number of positions $P_{t-1j}$ of the capsule-type endoscope 3 detected at the time t−1.

If the CPU 36 has determined at step S51 that the region $R_{xyztk}$ and the region $R_{xyzt-1j}$ are not adjacent to each other, it further determines if j<$N_j$ at step S54. If this condition is met, the CPU 36 increments j by one at step S52, and then performs the processing at step S51.

If the CPU 36 has determined that the region $R_{xyztk}$ and the region $R_{xyzt-1j}$ are adjacent to each other, the CPU 36, at step S53, stores the connection relation in which the region $R_{xyztk}$ and the region $R_{xyzt-1j}$ are adjacent to each other in the second memory in the memory 35. FIG. 17 is a diagram illustrating an example of the case where connection relations between the regions $R_{xyztk}$ and the regions $R_{xyzt-1j}$ are stored in the second memory by means of a two-dimensional array.

In FIG. 17, the relationship between the regions $R_{xyz}$, the times t and the parameters k are shown in a two-dimensional array to easily find out the connection relation of two regions $R_{xyztk}$ and $R_{xyzt-1j}$ at the times t and t−1 as to whether or not they are adjacent to each other. In FIG. 17, where they are arranged in a line in the temporal axis (vertical axis which is the direction in which the times are arrayed) direction, they are region adjacent to each other.

After performing the aforementioned processing at step S53, at the next step S54, the CPU 36 determines if $j<N_j$. Then, if the CPU 36 has determined that this condition is met, it performs the processing at step S52, and then returns to step S51.

After the processing is repeated until $j \leq N_j$ is reached as described above, $j>N_j$ is reached, and thus, the CPU 36 proceeds to the next step S55 via determination at step S54. The CPU 36, at step S55, determines if $k<N_k$, and if this condition is met, it increments k by one at the next step S56 and then returns to the processing at step S50.

As described above, the CPU 36 repeats the processing from steps S50 to S56. Then, upon $k>N_k$ being reached as a result of the processing at steps S50 to S56 being repeated, the CPU 36 proceeds to step S57 via determination at step S55.

At step S57, the CPU 36 determines if t<tend, and if this condition is met, it returns to step S48, and at step S48, sets t to t+1 and returns to step S43.

As described above, the CPU 36 repeats the processing from steps S43 to S57. Then, upon reaching a time not meeting the condition of t<tend, it terminates this processing.

Figure 18:
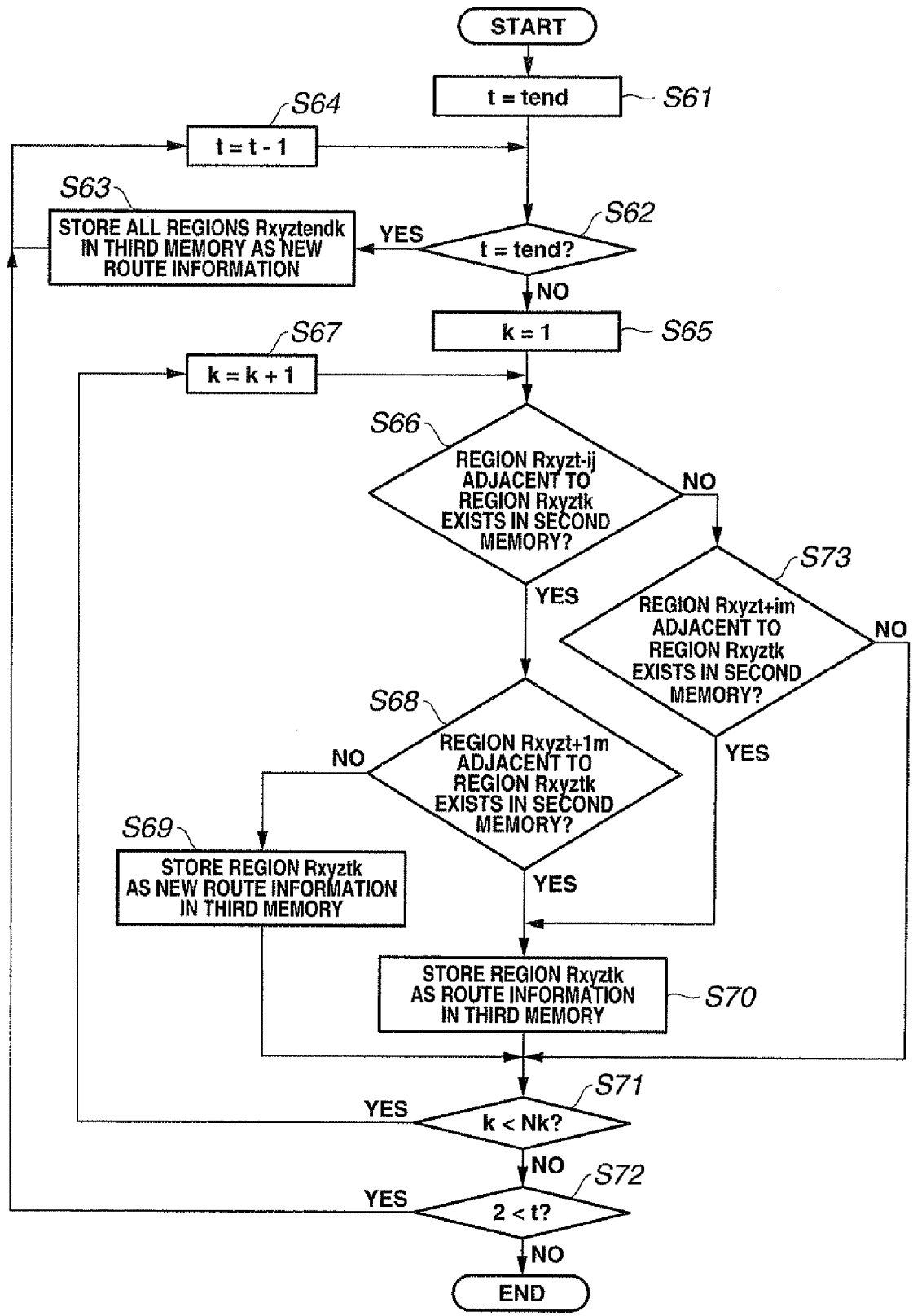
FIG. 18 is a flowchart of the content of processing for calculating a track after the processing in FIG. 16.

As a result of the processing at the aforementioned series of steps, information on all the connection relations at the adjacent times is stored in the second memory in the memory 35. Then, the CPU 36, as shown in FIG. 18, proceeds to processing for searching for a track from the connection relation information. Upon the start of this processing, at the first step S61, the CPU 36 sets the time for processing t to the last time tend, that is, t=tend.

The CPU 36, at step S62, determines if the condition of t=tend is met. Then, if this condition is met, the CPU 36, at step S63, regards information on the connection relations at the time tend to be new route information and stores all the regions $R_{xyztendk}$ (k=1, 2, 3 ...) stored in the second memory in the memory 35, in the third memory in the memory 35. Subsequently, the CPU 36, at step S64, sets the time t to a time one time before, that is, t=t−1 and returns to the processing at step S62.

At this step S62, the CPU 36 determines that the condition of t=tend is not met and proceeds to step S65, and sets the parameter k to k=1, and then proceeds to the next step S66.

At step S66, the CPU 36 determines whether or not any region $R_{xyzt-1j}$ adjacent to the region $R_{xyztk}$ exists in the second memory.

Then, if the CPU 36 determines that no such adjacent region exists, it proceeds to step S73, and further determines whether or not any region $R_{xyzt+1m}$ adjacent to the region $R_{xyztk}$ exists in the second memory. Here, m represents a parameter for, if multiple regions $R_{xyzt+1}$ exist at the time t+1, distinguishing such regions from one another.

Then, if the CPU 36 has determined that no such adjacent region exists, it proceeds to step S71. Meanwhile, if the CPU 36 has determined at step S73 that an adjacent region $R_{xyzt+1m}$ exists, it proceeds to step S70, and stores this information in the third memory as route information, and then proceeds to the next step S71.

Meanwhile, if the CPU 36 has determined at step S66 that an adjacent region $R_{xyzt-1j}$ exists, it proceeds to step S68, and further determines whether or not a region $R_{xyzt+1m}$ adjacent to the region $R_{xyztk}$ exists in the second memory. Here, m represent a parameter for, if multiple regions $R_{xyzt+1}$ exist for the time t+1, distinguishing them from one another.

If the CPU 36 has determined that no such adjacent region exists, at step S69, it stores that information in the third memory as new route information, and then returns to step S66 via the processing at step S67.

Meanwhile, if the CPU 36 has determined at step S68 that an adjacent region $R_{xyzt+1m}$ exists, it proceeds to step S70, and stores this information in the third memory as route information, and proceeds to the next step S71.

Then, at step S71, the CPU 36 determines if the condition of $k<N_k$ is met, if this condition is met, the CPU 36 returns to step S66 via step S67.

Meanwhile, if the CPU 36 has determined that the condition of $k<N_k$ is not met, it proceeds to the next step S72, and further determines if the condition of 2<t is met. Then, if this condition is met, the CPU 36 returns to step S62 via step S64.

Then, the CPU 36 sets the time to the time t−1 one time before and repeats similar processing. When the time t has become the first time t=1 as a result of that, the CPU 36 terminates this processing.

As a result of the above-described processing being performed, route information such as that shown in FIG. 19, for example, is stored in the third memory. In FIG. 19, the regions are included in the respective rows, and the row including the largest number of regions is extracted, and the temporal route, that is, the track of the capsule-type endoscope 3 is formed by connecting (joining) the regions for the respective times.

Alternatively, the CPU 36 may calculate the route (track) in such a manner as described below.

Where multiple adjacent regions exist, the CPU 36 calculates the minimum value of the cost values for the estimated positions in the respective regions (e.g., the sums of the squares of the residual differences between the measured values and the calculated values), and determines the extracted region with the smallest cost value to be the connected region.

The CPU 36 records the information on the estimated positions with the smallest cost values in the respective regions, together with the extracted regions and the connection information. Then, the CPU 36 ranks the routes according to the number of regions included in the routes, and calculates the lengths of the entire routes for the highly-ranked routes to calculate the route whose entire length is the shortest as a track. Also, the CPU 36 may calculate the route whose total sum of the cost values is the smallest to determine it to be a track.

The present embodiment provides the following advantageous effects.

According to the present embodiment, regions are set to reduce the number of positions to be estimated, enabling searching for routes at a speed higher than in embodiment 1. Besides, likewise in embodiment 1, the positions and track of the capsule-type endoscope 3 can be estimated with high accuracy.

Embodiment 3

Next, embodiment 3 of the present invention will be described. The configuration of the present embodiment is similar to that of embodiment 1, and is different from that of embodiment 1 in the content of processing provided by the program in the track estimating section. In the present embodiment, the CPU 36 performs track estimation processing using the Dijkstra method as described below.

Next, the operation of the present embodiment will be described. The operation is similar to that of embodiment 1 or 2 up to the steps of calculating and recording the estimated positions or regions and the connection information. In the present embodiment, the Dijkstra method is employed as a technique for determining routes. This Dijkstra method is described in, e.g., "Data Structures and Algorithms" (coauthored by Nobuo Saito and Seiichi Nishihara, Corona Publishing Co., Ltd., pp. 124-129).

In the Dijkstra method, for example, in embodiment 1, the processing for setting a plurality of routes connecting the positions estimated at the respective adjacent times t and t−1 from the time t=1 to tend via lines L using such positions as nodes is performed.

Then, the CPU 36 properly assigns weights to, e.g., the lengths of the lines L for them (as a matter of course, the same weight may be assigned as 1), calculates the accumulated value (cost value) obtained by adding up the values in the route for all possible routes, and determines the route whose accumulated value (cost value) is the smallest to be the final route, that is, the track.

In the present embodiment, the CPU 36, upon the estimation of the positions, performs the processing for calculating cost values for them and comparing the calculated cost values to calculate the final route. Thus, the present embodiment provides the following advantageous effect.

In the present embodiment, the use of the Dijkstra method enables search for routes at a speed higher than in embodiment 1 or 2.

Embodiment 4

Next, embodiment 4 of the present invention will be described. The configuration of the present embodiment is similar to that of embodiment 1, and different from that of embodiment 1 in the content of processing provided by the program in the track estimating section.

For the operation of the present embodiment, the CPU 36, where a route from the starting point and the endpoint is disconnected in the middle, connects the disconnected routes so that the distance between the endpoint of one route and the starting point of the other route is as short as possible.

As an advantageous effect of the present embodiment, it is possible to search for a route from the starting point to the endpoint even if the route is disconnected in the middle.

Embodiment 5

Next, embodiment 5 of the present invention will be described. The configuration of the present embodiment is similar to that of embodiment 1, and different from that of embodiment 1 in the content of processing provided by the program in the track estimating section.

For the operation of the present embodiment, the CPU 36 constrains estimated positions/regions from forecast information relating to a site of a living body. For example, in a site such as esophagus, the capsule-type endoscope 3 can be considered to move substantially linearly from the mouth to the stomach, and accordingly, it is almost possible to forecast estimated positions, and the estimated positions outside the forecasted area are excluded from the targets of the processing by the CPU 36.

Also, since the moving direction of the capsule-type endoscope (direction from the mouth toward the stomach) can be forecasted, when connecting the estimated positions or regions, the connections from the stomach toward the mouth are excluded from the targets of the processing by the CPU 36.

As an advantageous effect of the present embodiment, it is possible to search routes at high speed.

Embodiment 6

Next, embodiment 6 of the present invention will be described. The configuration of the present embodiment is similar to that of embodiment 1, and different from that of embodiment 1 in the content of processing provided by the program in the track estimating section.

Next, the operation of the present embodiment will be described.

Multiple positions of the capsule-type endoscope 3 may be estimated depending on the number and arrangement of antennae 11 for reception, the manner to provide an initial value for the position $(x_{wg}, y_{wg}, z_{wg})^{(0)}$ of the antenna 23, and noise, etc. Since the capsule-type endoscope 3 makes relative small movements in a body cavity and picks up images at short intervals, the position of the capsule-type endoscope 3 estimated at a certain time and the position of the capsule-type endoscope 3 estimated at a time immediately before or after the certain time can be considered to be positions that are substantially the same or close to each other.

Accordingly, the CPU 36 connects multiple positions of the capsule-type endoscope 3 estimated at temporally adjacent times using the distance or cost values, etc., as a condition, to calculate the positions of the capsule-type endoscope 3 at the respective times from the entire connection state.

The CPU 36, as shown in FIG. 8, sets positions estimated at a time t−1 to P(t−1)j (j=1, 2, . . . Nj), and positions estimated at a time t to Pti (i=1, 2, . . . , Ni). Also, the CPU 36 sets an evaluation function $h_{(t-1)j,ti}$ for the positions P(t−1)j and Pti estimated at the times t−1 and t as described below.

$$h_{(t-1)j,ti} = d_{(t-1)j,ti} + w(\cos t_{(t-1)j} + \cos t_{ti})$$

$$d_{(t-1)j,ti} = [(P_{xti} - P_{x(t-1)j})^2 + (P_{yti} - P_{y(t-1)j})^2 + (P_{zti} - P_{z(t-1)j})^2]^{1/2},$$

provided that $d_{(t-1)j,ti}$ indicates the distance between the respective estimated positions, and $cost_{(t-1)j}$ and $cost_{ti}$ indicates the cost values obtained when the positions are estimated, and w indicates a weighting factor. This w is calculated from, for example, a distance of 3 cm and a value obtained by tripling the minimum cost $cost_{min}$ at the time of the position estimation.

In other words, $$w = 0.03/(3 cost_{min})$$

The CPU 36 calculates an evaluation function for all the combination of the positions P(t−1)j and Pti estimated at the times t−1 and t. Then, the CPU 36 arranges the position combinations in ascending order of value according to the evaluation function, and extracts the high-order combinations from those with the smallest values in that case and stores them.

For example, the CPU 36 sets a threshold value for the evaluation function, and where a value according to the evaluation function is equal to or larger than the threshold value, the CPU 36 does not store the connection information and the value according to the evaluation function. Also, where there is a large distance, e.g., a distance of 5 cm or more, between two points, the CPU 36 cancels the calculation according to the evaluation function and does not store the connection information, etc.

Lastly, the CPU 36 connects the estimated positions at the respective times according to the connection information with the position of the capsule-type endoscope 3 stored together with the connection information as the starting point, and calculates the total sum of the values according to the evaluation function. The CPU 36 extracts the route whose connection is the longest to calculate the track as the positions of the capsule-type endoscope 3 at the respective times. Also, where multiple routes are calculated, the CPU 36 estimates the positions of the capsule-type endoscope 3 at the respective times from the route whose sum of the values according to the evaluation function is small. Where all the routes are disconnected in the middle (e.g., all the values according to the evaluation function are equal or larger than the threshold value, or the distances are 5 cm or more), the CPU 36 performs processing similar to the above-described processing with the position at the time when the route is disconnected as the starting point, and the connection between the disconnection parts, as in the embodiment 4, is made so that the distance between the endpoint of one route and the starting point of the other route is as short as possible.

The CPU 36 calculates an value according to the evaluation function for all the combinations of the positions P(t−1)j and Pti at the times t−1 and t. Then, the CPU 36 arranges the position combinations in ascending order of value according to the evaluation function, and extracts the high-order combinations from those with the smallest values in that case and stores them.

For example, the CPU 36 sets a threshold value for the evaluation function, and where a value according to the evaluation function is equal to or larger than the threshold value, the CPU 36 does not store the connection information and the value according to the evaluation function. Also, where there is a large distance, e.g., a distance of 5 cm or more, between two points, the CPU 36 cancels the calculation according to the evaluation function and does not store the connection information, etc.

The present embodiment provides the following advantageous effect.

According to the present embodiment, even where multiple positions of the capsule-type endoscope 3 have been estimated depending on the number and arrangement of antennae 11 for reception, the manner to provide the position $(x_{wg}, y_{wg}, z_{wg})^{(0)}$ of an initial value for an antenna 23, and noise, etc., the position of the capsule-type endoscope 3 can uniquely be determined. Also, according to the present embodiment, since an evaluation function is set using the distance between two points and the cost values, the correct positions of the capsule-type endoscope 3 can be estimated using this evaluation function.

Embodiment 7

Next, embodiment 7 of the present invention will be described. The configuration of the present embodiment is similar to that of embodiment 1, and is different from that of embodiment 1 in the content of processing provided by the program in the track estimating section.

Next, the operation of the present embodiment will be described.

As described above, FIG. 13B a diagram illustrating a state in which a space where the capsule-type endoscope 3 exists is divided into a plurality of regions $R_{XYZ}$ (x=1, 2, 3, . . . , y=1, 2, 3, . . . , and z=1, 2, 3, . . . ). Also, FIG. 14 is a diagram illustrating respective positions P(t−1)j (j=1, 2, 3, . . . ) and Pti (i=1, 2, 3, . . . ) estimated as positions of the capsule-type endoscope 3 from multiple output values of the antennae 11 obtained at times t−1 and t.

The CPU 36 calculates regions $R_{xyz}$ including the positions Pti (i=1, 2, 3, . . . ) estimated at the time t. Also, when the CPU 36 connects them with the regions obtained at the time t−1, it calculates the following evaluation function.

$$h_{(t-1)j,ti} = d_{(t-1)j,ti} + w_1(\cos t_{(t-1)j} + \cos t_{ti}) + w_2/(n_{Qlmn} + n_{Qlm+1n})$$

$$d_{(t-1)j,ti} = [(Q_{xlmn} - Q_{xlm+1n})^2 + (Q_{ylmn} - Q_{ylm+1n})^2 + (Q_{zlmn} - Q_{zlm+1n})^2]^{1/2},$$

provided that $d_{(t-1)j,ti}$ indicates the distance between the barycentric positions $Q_{t-1}$ and $Q_t t$ of regions $R_{xyz}$ including respective estimated positions, and $\cos t_{(t-1)j}$ and $\cos t_{ti}$ indicate cost values obtained when positions are estimated, and also, $w_1$ and $w_2$ indicate weighting factors. For example, $w_1$ is a value calculated from a distance of 3 cm and a value obtained by tripling the minimum cost at the time of the position estimation, and $w_2$ is a value calculated from the number of divided regions and the number ($n_{Qlmn}$, $n_{Qlm+1n}$) of estimated positions included in each of the relevant region.

In other words, the weighting factors $w_1$ and $w_2$ are values that can be expressed as follows:

$$w1 = 0.03/(3\cos t_{min})$$

$$w2 = 1000.0$$

The CPU 36 determines the connection relations of the estimated positions at the times t and t−1, which have been extracted based on the valuation function, in the divided regions. The connections are limited to those for movements between adjacent regions. Also, where there are multiple adjacent regions, the region including the largest number of estimated positions is determined to be the connected region. FIG. 15 shows a state of connection from a region obtained at the time t to that obtained at the time t−1. The CPU 36 records information on the region obtained at the time t−1 connected to the region obtained at the time t. Furthermore, the CPU 36 records extracted positions and connection information for all the recorded data.

The CPU 36, as in embodiment 2, sets the region stored at the last to be a stating point, and the region stored at the first to be an endpoint, and calculates routes from the starting point to the endpoint using the connection information stored together with the extracted regions. The CPU 36 calculates the route including the largest number of regions and determines the estimated positions at the respective times from the obtained route. Also, the estimated positions in this case are the center positions (barycentric positions) of the regions.

Where there are multiple adjacent regions, the CPU 36 calculates the minimum value in the cost values (e.g., the sums of the squares of the residual differences between the measured values and the calculated values) of the estimated positions included in the respective regions, and determines the extracted region with the smallest cost value to be the connected region.

Then, the CPU 36 records the information on the estimated positions whose cost values are the smallest in the respective regions together with the extracted regions and the connection information. Furthermore, the CPU 36 ranks the routes according to the number of regions included in the routes, and calculates the lengths of the entire routes for the highly-ranked routes to calculate the route whose entire length is the shortest. Also, the CPU 36 may calculate the route whose total sum of the cost values is the smallest.

The present embodiment provides the following advantageous effect.

According to the present embodiment, regions are set to reduce the number of positions to be estimated, enabling search for routes at a speed higher than in embodiment 1.

In the above-described embodiments, etc., in addition to the estimated positions of the antenna 23 (or the capsule-type endoscope 3), information on the directions thereof may be used for the processing for calculating a track. The use of information on the directions as mentioned above enables calculation of a track and positions with higher accuracy or with higher reliability compared to the case where only the positions are used.

In the above-described embodiments, an embodiment formed by, e.g., combining parts of different embodiments also falls under the scope of the present invention. Also, an embodiment partially modified without departing from the scope and spirit of the present invention also falls under the scope of the present invention.

Although the above-described examples have been described for the case where information on images of a body cavity optically picked up is acquired as information on the inside of a living body, the present invention is not limited thereto, and can also be employed in a capsule-type medical device for pH calculation by providing a pH sensor to the device. Alternatively, a medicinal solution and mean for spraying the medicinal solution may be provided to provide medical treatment.

What is claimed is:

1. A capsule-type medical device comprising:
    a capsule-type in-vivo device including an antenna, the capsule-type in-vivo device being inserted into a living body;
    a wireless transmission section for transmitting wirelessly an electromagnetic wave signal from the antenna in the capsule-type in-vivo device;
    a plurality of extracorporeal antennae arranged outside the living body;
    an estimation section for estimating a position of the antenna or the capsule-type in-vivo device from the electromagnetic wave signal at a time when the electromagnetic wave signal was received by the plurality of extracorporeal antennae; and
    a track calculating section for calculating a track of movement of the capsule-type in-vivo device according to a condition set for the case where a plurality of positions at mutually different times have been estimated by the estimation section;
    wherein the track calculating section defines an evaluation function for two temporally adjacent estimated positions, the evaluation function including information on a distance between the two positions and estimation information obtained when the two positions are estimated, and calculates the track, employing a value according to the evaluation function being equal to or lower than a predetermined value, as the condition.

2. The capsule-type medical device according to claim 1, wherein the capsule-type in-vivo device includes image pickup section for picking up an image of a subject in the living body.

3. The capsule-type medical device according to claim 1, wherein, when the track calculating section calculates the track between a position which is a starting point estimated at a first time and a position which is an endpoint estimated at a last time so as to include the two positions at which the evaluation function is equal to or lower than the predetermined value, the track calculating section calculates the track, employing a total sum value of the evaluation function set according to the track between the starting point and the endpoint being equal to or lower than a second predetermined value, as a second condition.

4. The capsule-type medical device according to claim 1, wherein the track calculating section sets, as the evaluation function, a sum of the information on the distance between the two positions and a value obtained by multiplying a sum of cost values of the two positions as the estimation information obtained when the two positions are estimated by a weighting factor, each of the cost values being a square of a residual difference between a measured value and an estimation value.

* * * * *